United States Patent [19]
Ognyanov et al.

[11] Patent Number: 6,162,824
[45] Date of Patent: Dec. 19, 2000

[54] TRICYLIC AMINO-ACID DERIVATIVES

[75] Inventors: Vassil I. Ognyanov, Princeton; Allen Hopper, Somerset, both of N.J.; Stanley Charles Bell, Narberth, Pa.; Eric A. Meade, Fanwood, N.J.; Michael De Vivo, New York, N.Y.

[73] Assignee: Allelix Neuroscience Inc.

[21] Appl. No.: 09/365,070

[22] Filed: Jul. 30, 1999

[51] Int. Cl.[7] .................. A61K 31/38; A61K 31/195; C07D 333/22; C07C 211/00
[52] U.S. Cl. .................. 514/438; 514/567; 549/77; 564/433
[58] Field of Search .................. 564/433; 549/77; 514/567, 438

[56] References Cited
U.S. PATENT DOCUMENTS 4,818,704  4/1989  Josefsson et al. .................. 436/111

(List continued on next page.)

OTHER PUBLICATIONS

Zee–Cheng et al, CA72:133161, 1970.
Koenig et al, CA 68:69299, 1968.

*Primary Examiner*—Deborah C. Lambkin
*Attorney, Agent, or Firm*—Dechert

[57] ABSTRACT

Described herein are compounds which have the general formula:

I

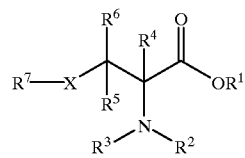

or a prodrug or pharmaceutically acceptable salt, solvate or hydrate thereof wherein:
$R^1$ is selected from the group consisting of H, alkyl and the counter ion for a basic addition salt;
X is selected from the group consisting of $CR^9R^{10}$, S, O, SO, $SO_2$, NH and N-alkyl;
$R^2$, $R^3$, $R^4$, $R^9$ and $R^{10}$ are independently selected from the group consisting of H and alkyl;
$R^5$ and $R^6$ are independently selected from the group consisting of H, alkyl and phenyl, or, alternatively, $R^5$ and $R^6$ together may form a methylene group or a 3- to 6-membered a spirocyclic group;
wherein, when X is $CR^9R^{10}$, one or both pairs of $R^5$ and $R^9$ or $R^6$ and $R^{10}$ may join to form a double or triple bond
$R^7$ is selected from the group consisting of Formula II–V:

II

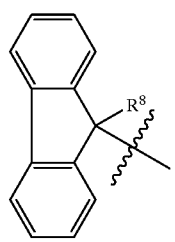

III

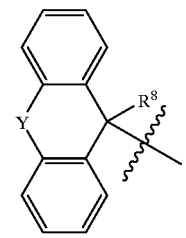

IV

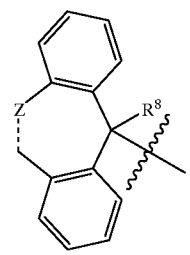

V
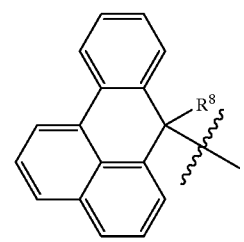

which are all optionally substituted, at nodes other than $R^8$, with 1–4 substituents independently selected from the group consisting of alkyl, halo, aryl (which may be substituted as for $R^8$), trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2NHalkyl$, —$SO_2N(alkyl)_2$ and 1,2-methylenedioxy; and wherein any of the benzo-fused rings in structures II to V may be replaced by a 5- or 6-membered heterocyclic ring selected from the group consisting of pyridine, thiophene, furan and pyrrole;
wherein $R^8$ is selected from the group consisting of H, alkyl, benzyl, cycloalkyl, indanyl and an optionally substituted aryl group, wherein the optional substituents are independently selected from 1–4 members of the group consisting of alkyl, halo, aryl, trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2NHalkyl$, —$SO_2N(alkyl)_2$ and 1,2-methylenedioxy;
—represents a single or double bond;
Y is selected from the group consisting of O, S, SO, NH, N-alkyl, $CH_2$, CH-alkyl, $C(alkyl)_2$, and C=O;
Z is selected from the group consisting of $CH_2$, O, S, NH and N-alkyl when—is a single bond;
Z is selected from the group consisting of CH and N when—is a double bond.

Also described is the use of these compounds as pharmaceuticals.

19 Claims, No Drawings

6,162,824

FOREIGN PATENT DOCUMENTS

| | | | |
|---|---|---|---|
| 5,017,589 | 5/1991 | Kawamura et al. | 514/532 |
| 5,079,260 | 1/1992 | Weitzberg et al. | 514/532 |
| 5,101,059 | 3/1992 | Carpino et al. | 549/388 |
| 5,294,522 | 3/1994 | Uchida et al. | 430/345 |
| 5,679,694 | 10/1997 | Franzmann et al. | 514/339 |
| 5,763,609 | 6/1998 | Yuan et al. | 544/363 |
| 5,849,781 | 12/1998 | Langlois et al. | 514/411 |
| 5,856,341 | 1/1999 | Bell et al. | 514/324 |
| 5,942,641 | 8/1999 | Tanaka et al. | 560/139 |
| 5,994,364 | 11/1999 | Njoroge et al. | 514/290 |
| 5,998,461 | 12/1999 | Lesieur et al. | 514/411 |

TRICYLIC AMINO-ACID DERIVATIVES

The present invention relates to a class of substituted amino acids, pharmaceutical compositions and methods of treating neurological and neuropsychiatric disorders.

Synaptic transmission is a complex form of intercellular communication that involves a considerable array of specialized structures in both the pre- and post-synaptic terminal and surrounding glial cells (Kanner and Schuldiner, *CRC Critical Reviews in Biochemistry*, 22, 1987:1032). Transporters sequester neurotransmitter from the synapse, thereby regulating the concentration of neurotransmitter in the synapse, as well as its duration therein, which together influence the magnitude of synaptic transmission. Further, by preventing the spread of transmitter to neighbouring synapses, transporters maintain the fidelity of synaptic transmission. Lastly, by sequestering released transmitter into the presynaptic terminal, transporters allow for transmitter reutilization.

Neurotransmitter transport is dependent upon extracellular sodium and the voltage difference across the membrane; under conditions of intense neuronal firing, as, for example, during a seizure, transporters can function in reverse, releasing neurotransmitter in a calcium-independent non-exocytotic manner (Attwell et al., *Neuron*, 11, 1993:401–407). Pharmacologic modulation of neurotransmitter transporters thus provides a means for modifying synaptic activity, which provides useful therapy for the treatment of neurological and psychiatric disturbances.

The amino acid glycine is a major neurotransmitter in the mammalian central nervous system, functioning at both inhibitory and excitatory synapses. By nervous system, both the central and peripheral portions of the nervous system are intended. These distinct functions of glycine are mediated by two different types of receptor, each of which is associated with a different class of glycine transporter. The inhibitory actions of glycine are mediated by glycine receptors that are sensitive to the convulsant alkaloid strychnine, and are thus referred to as "strychnine-sensitive". Such receptors contain an intrinsic chloride channel that is opened upon binding of glycine to the receptor; by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions.

Glycine also functions in excitatory transmission by modulating the actions of glutamate, the major excitatory neurotransmitter in the central nervous system. See Johnson and Ascher, *Nature*, 325, 1987:529–531; Fletcher et al., *Glycine Transmission*, Otterson and Storm-Mathisen, eds., 1990:193–219. Specifically, glycine is an obligatory co-agonist at the class of glutamate receptor termed N-methyl-D-aspartate (NMDA) receptor. Activation of NMDA receptors increases sodium and calcium conductance, which depolarizes the neuron, thereby increasing the likelihood that it will fire an action potential. NMDA receptors are widely distributed throughout the brain, with a particularly high density in the cerebral cortex and hippocampal formation.

Molecular cloning has revealed the existence in mammalian brains two classes of glycine transporters, termed GlyT-1 and GlyT-2. GlyT-1 is found throughout the brain and spinal cord, and it has been suggested that its distribution corresponds to that of glutamatergic pathways and NMDA receptors (Smith, et al., *Neuron*, 8, 1992:927–935). Molecular cloning has further revealed the existence of three variants of GlyT-1, termed GlyT-1a, GlyT-1b and GlyT-1c. Two of these variants (1a and 1b) are found in rodents, each of which displays a unique distribution in the brain and peripheral tissues (Borowsky et al., *Neuron*, 10, 1993:851–863; Adams et al., *J. Neuroscience*, 15, 1995:2524–2532). The third variant, 1c, has only been detected in human tissues (Kim, et al., *Molecular Pharmacology*, 45, 1994:608–617). These variants arise by differential splicing and exon usage, and differ in their N-terminal regions. GlyT-2, in contrast, is found predominantly in the brain stem and spinal cord, and its distribution corresponds closely to that of strychnine-sensitive glycine receptors (Liu et al., *J. Biological Chemistry*, 268, 1993:22802–22808; Jursky and Nelson, *J. Neurochemistry*, 64, 1995:1026–1033). Another distinguishing feature of glycine transport mediated by GlyT-2 is that it is not inhibited by sarcosine as is the case for glycine transport mediated by GlyT-1. These data are consistent with the view that, by regulating the synaptic levels of glycine, GlyT-1 and GlyT-2 selectively influence the activity of NMDA receptors and strychnine-sensitive glycine receptors, respectively.

Compounds which inhibit or activate glycine transporters would thus be expected to alter receptor function and, thus, provide therapeutic benefits in a variety of disease states.

For example, inhibition of GlyT-2 can be used to increase the activity of inhibitory neurons having strychnine-sensitive glycine receptors via increasing synaptic levels of glycine, thus diminishing the transmission of pain-related (i.e. nociceptive) information in the spinal cord, which has been shown to be mediated by these receptors (Yaksh, *Pain*, 37, 1989:111–123). Additionally, enhancing inhibitory glycinergic transmission through strychnine-sensitive glycine receptors in the spinal cord can be used to decrease muscle hyperactivity, which is useful in treating diseases or conditions associated with increased muscle contraction, such as spasticity (Truong et al., *Movement Disorders*, 3, 1988:77–89; Becker, *FASEB J*, 4, 1990:2767–2774). Spasticity associated with stroke, head trauma, multiple sclerosis, spinal cord injury, dystonia, and other conditions of illness and injury of the nervous system (such as epilepsy) can be treated via modulation of glycine transporters.

Gamma-amino butyric acid (GABA) is the predominant inhibitory neurotransmitter of the central nervous systems and is widely distributed therein. The ionotropic GABAA and GABA, receptors and the metabotropic $GABA_B$ receptors mediate GABA activity. $GABA_A$ and $GABA_C$ receptors inhibit neuronal membrane excitability by causing a chloride influx, resulting in hyperpolarization of the neuron. $GABA_B$ receptors are coupled to guanine nucleotide binding proteins (G-proteins). If the G-protein is of the type $G_i$, receptor activation causes the opening of potassium channels, leading to membrane hyperpolarization. If the G-protein is of the class $G_O$, receptor activation retards the opening of calcium channels. $GABA_B$ receptors are commonly found on presynaptic membranes in glutamatergic axon terminals, where the retardation of calcium channel opening inhibits the depolarization-dependent release of glutamate from axon terminals (Costa, *Annu. Rev. Pharmacol. Toxicol.* 38, 1998:321–350).

GABA signaling is terminated by the re-uptake of GABA by GABA transporters. Four such transporters have been identified, GAT-1, -2 and -3, and BGT-1 (which also transports betaine) (Miller, Kleven et al., *Neurotransmitter Transporters: Structure, Function, and Regulation*, Reith ed. 1997:101–150). The GABA transporters are members of the sodium- and chloride-dependent group of transporter gene families. Only GAT-1 and GAT-3 are preferentially localized to the CNS, whereas GAT-2 and BGT-1 are found both in CNS and non-CNS tissues (Ikegaki et al., *Mol. Brain Res.* 26, 1994:47–54, Borden et al., *J. Neurochem.* 64, 1995:977–984, Borden et al., *J. Biol. Chem.* 267, 1992:21098–21104, Liu et al, *J. Biol. Chem.* 268, 1993:2106–2112, Clark et al., *Neuron* 9, 1992:337–348).

Similar to the glycine transporter, compounds which inhibit or enhance the activity of GABA transporters will alter the function of GABA receptors, and, thus, prove useful in the treatment of a variety of disease states.

GABA transmission has been successfully exploited as a target to yield drugs such as benzodiazepines and barbiturates ($GABA_A$ receptor modulators), baclofen ($GABA_B$ receptor agonist) and vigabatrin (GABA transaminase inhibitor). GABA transport modulators will be effective in the treatment of indications for which such compounds have been used, including use as anti- anxiety drugs, anti-epileptics, muscle relaxants and anti-convulsants. For example, the GAT-1 inhibitor, Tiagabine, is marketed as an anticonvulsant.

GABA transport inhibitors will also be useful for the treatment of pain. For example, GABA re-uptake inhibitors have demonstrated analgesic activity and were reported to be more potent than GABA receptor agonists (Zorn and Enna. *Life Sci.* 37 1985:1901–1912). Both GAT-1 and GAT-3 mRNAs were detected in rat in neurons of the periaqueductal gray and spinal cord dorsal horn, and in the thalamus, consistent with a role in nociception (Durkin, MM et al. *Mol Brain Res.* 33 1995:7–21).

Evidence also suggests that low GABA levels are linked to depression and possibly mania (Reviewed in Shiah I. S. and Yatham L. N., *Life Sciences* 63 1998:1289–1303). Animal models of depression indicate a functional correlation of depression with decreased GABA levels. Furthermore, there is some data to suggest that antidepressants like Prozac (Fluoxetine) may, in addition to blocking serotonin uptake, cause an increase in endogenous substances that activate GABA receptors (Uzunove, Sheline et al. *Proc. Natl. Acad. Sci. USA* 95 1990:3239–3244). Thus, compounds which inhibit GABA transport will also be useful for the treatment of depression.

Schizophrenia and other psychoses may have a common link in altered GABA neurotransmission (Keverne, *Brain Res. Bulletin* 48 1999:467–473), suggesting that compounds which alter GABA uptake will be effective antipsychotic agents.

Given that both glycine and GABA are inhibitory neurotransmitters, and that their expression overlaps in many areas of the CNS, compounds with dual activity on both glycine and GABA transporters will be more efficacious than compounds specific for either transporter alone. For example, there is an overlap in expression of GABA, glycine and their receptors in the spinal cord (Todd, A. J. et al., *J. Neuroscience* 16 1996:974–982). A pain-relieving drug which acts at both glycine and GABA transporters will be more effective than a drug which blocks only one of these. In addition, glycine and GABA are implicated in schizophrenia: a compound with dual activity at both glycine and GABA transporters will be a more useful therapeutic agent than a compound which interacts with only one transporter.

Similarly, compounds which inhibit glycine transport via both the GlyT-1 and GlyT-2 glycine transporters will be more effective (in the treatment of, for example, pain and spasticity) than compounds which act at only one of these transporters.

SUMMARY OF THE INVENTION

According to one aspect of the invention, there are provided compounds which inhibit glycine transport via the GlyT-2 transporters, or are precursors, such as prodrugs, to compounds that inhibit such transport. Thus, the invention provides a class of compounds of Formula 1:

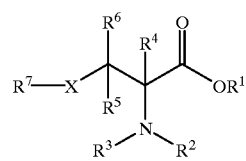

I or a prodrug or pharmaceutically acceptable salt, solvate or hydrate thereof wherein:

$R^1$ is selected from the group consisting of H, alkyl and the counter ion for a basic addition salt;

X is selected from the group consisting of $CR^9R^{10}$, S, O, SO, $SO_2$, NH and N-alkyl;

$R^2$, $R^3$, $R^4$, $R^9$ and $R^{10}$ are independently selected from the group consisting of H and alkyl;

$R^5$ and $R^6$ are independently selected from the group consisting of H, alkyl and phenyl, or, alternatively, $R^5$ and $R^6$ together may form a methylene group or a 3- to 6-membered spirocyclic group;

wherein, when X is $CR^9R^{10}$, one or both pairs of $R^5$ and $R^9$ or $R^6$ and $R^{10}$ may be linked to form a double or triple bond;

$R^7$ is selected from the group consisting of Formula II–V:

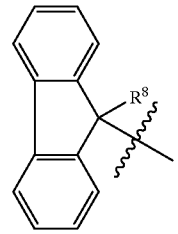

II

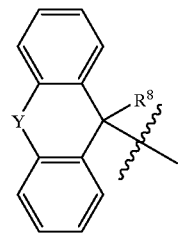

III

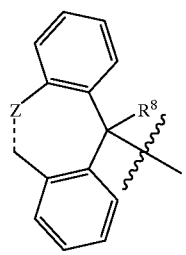

IV

V

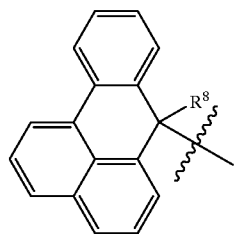

which are all optionally substituted, at nodes other than $R^8$, with 1–4 substituents independently selected from the group consisting of alkyl, halo, aryl (which may be substituted as for $R^8$), trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2NHalkyl$, —$SO_2N(alkyl)_2$ and 1,2-methylenedioxy; and wherein any of the benzo-fused rings in structures II to V may be replaced by a 5- or 6-membered heterocyclic ring selected from the group consisting of pyridine, thiophene, furan and pyrrole;

$R^8$ is selected from the group consisting of H, alkyl, benzyl, cycloalkyl, indanyl and an optionally substituted aryl group, wherein the optional substituents are independently selected from 1–4 members of the group consisting of alkyl, halo, aryl, trifluoromethyl, trifluoromethoxy, nitro, cyano, amino, mono-alkylamino, di- alkylamino, alkoxycarbonyl, alkylcarbonyl, alkoxythiocarbonyl, alkylthiocarbonyl, alkoxy, alkylS-, phenoxy, —$SO_2NH_2$, —$SO_2NHalkyl$, —$SO_2N(alkyl)_2$ and 1,2-methylenedioxy; —represents a single or double bond;

Y is selected from the group consisting of O, S, SO, NH, N-alkyl, $CH_2$, CH-alkyl, $C(alkyl)_2$, and C=O;

Z is selected from the group consisting of $CH_2$, O, S, NH and N-alkyl when—is a single bond; and Z is selected from the group consisting of CH and N when—is a double bond;

and with the provisos that, for compounds where the groups of Formula II to V contain only benzo-fused rings:

when X is S, $R^8$ is not H;

when X is S and $R^7$ is a group of Formula II, then $R^8$ is not optionally substituted phenyl; and when X is S and $R^7$ is a group of Formula III with X=O, then $R^8$ is not unsubstituted phenyl.

Compounds of the invention inhibit glycine transport. Certain compounds of the invention inhibit such transport via both the GlyT-1 and GlyT-2 transporters. Still other compounds of the invention inhibit the uptake of γ-aminobutyric acid (GABA) via GAT transporters, in particular via GAT-1, as well as glycine uptake via the GlyT-2 transporter. Preferred are those compounds which selectively inhibit glycine transport, and which do so via the GlyT-2 transporter. By GlyT-2 we mean those glycine transporters found predominantly in the brain stem and spinal cord and the distribution of which corresponds closely to that of strychnine-sensitive glycine receptors (Liu et al. *J. Biological Chemistry*, 268, 1993:22802–22808; Jursky and Nelson, *J. Neurochemistry*, 64, 995:1026–1033).

According to another aspect of the invention there is provided a pharmaceutical composition comprising a compound of Formula VI, or a prodrug or pharmaceutically acceptable salt, solvate or hydrate thereof, in an amount effective to inhibit glycine transport, and a pharmaceutically acceptable carrier.

VI

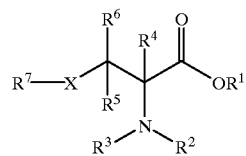

wherein:
$R^1$ is selected from the group consisting of H, alkyl and the counter ion for a basic addition salt;
X is selected from the group consisting of $CR^9R^{10}$, S, O, SO, $SO_2$, NH and N-alkyl;
$R^2$, $R^3$, $R^4$, $R^9$ and $R^{10}$ are independently selected from the group consisting of H and alkyl;
$R^5$ and $R^6$ are independently selected from the group consisting of H, alkyl and phenyl, or, alternatively, $R^5$ and $R^6$ together may form a methylene group or a 3- to 6-membered spirocyclic group;
wherein, when X is $CR^9R^{10}$, one or both pairs of $R^5$ and $R^9$ or $R^6$ and $R^{10}$ may join to form a double or triple bond;
$R^7$ is selected from the group consisting of Formula II–V:

II

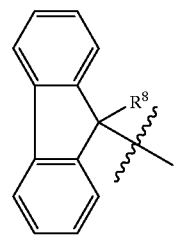

III

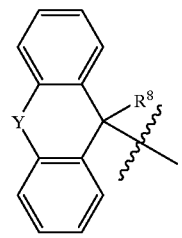

IV

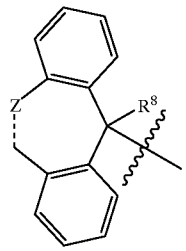

V

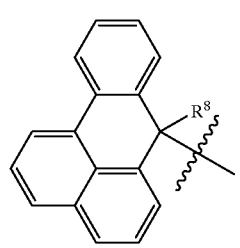

which are all optionally substituted, at nodes other than $R^8$, with 1–4 substituents independently selected from the group consisting of alkyl, halo, aryl (which may be substituted as for $R^8$), trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2NH$alkyl, —$SO_2N(alkyl)_2$ and 1,2-methylenedioxy; and wherein any of the benzo-fused rings in structures 11 to V may be replaced by a 5- or 6-membered heterocyclic ring selected from the group consisting of pyridine, thiophene, furan and pyrrole;

wherein $R^8$ is selected from the group consisting of H, alkyl, benzyl, cycloalkyl, indanyl and an optionally substituted aryl group, wherein the optional substituents are independently selected from 1–4 members of the group consisting of alkyl, halo, aryl, trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2NH$alkyl, —$SO_2N(alkyl)_2$ and 1,2-methylenedioxy;

—represents a single or double bond;

Y is selected from the group consisting of O, S, SO, NH, N-alkyl, $CH_2$, CH-alkyl, $C(alkyl)_2$, and C=O;

Z is selected from the group consisting of $CH_2$, O, S, NH and N-alkyl when—is a single bond; and Z is selected from the group consisting of CH and N when—is a double bond;

In another aspect of the present invention there are provided compositions containing a compound of Formula VI in amounts for pharmaceutical use to treat medical conditions for which a glycine transport inhibitor is indicated. Preferred are those compositions containing compounds useful in the treatment of medical conditions for which GlyT-2-mediated inhibition of glycine transport is needed, such as the treatment of pain, epilepsy or diseases or conditions associated with increased muscle contraction.

The use of compounds having mixed activity (i.e. compounds which inhibit glycine transport via both the GlyT-1 and GlyT-2 transporters, or compounds which inhibit the uptake of γ-aminobutyric acid (GABA) via GAT transporters as well as glycine uptake via the GlyT-2 transporter) also form aspects of the present invention. For example, compounds having mixed GlyT-2 and GAT activity are useful in the treatment of epilepsy. Compounds having mixed GlyT-1 and GlyT-2 activity are useful in the treatment of pain.

Definitions

The term "alkyl" as used herein means straight and branched chain alkyl radicals containing from one to six carbon atoms and includes methyl, ethyl, propyl, isopropyl, t-butyl, n-hexyl and the like.

The term "alkoxy" as used herein means branched chain alkoxy radicals containing from one to six carbon atoms and includes methoxy, ethoxy, propyloxy, isopropyloxy, t-butoxy and the like.

The term "cycloalkyl" as used herein means saturated carbocycles containing from 3–7 carbon atoms and includes cyclopropyl, cyclohexyl and the like. The term "aryl" as used herein means an aromatic or heteroaromatic, 5–10-membered mono- or bicyclic group and includes phenyl, naphthyl, furyl, pyridyl, indolyl, thiazolyl, imidazolyl and the like.

The term "1,2-methylenedioxy" as used herein means "—O—$CH_2$—O—" attached to adjacent nodes of a ring.

The term halo as used herein means halogen and includes fluoro, chloro, bromo and the like.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formulae I and VI or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

A "pharmaceutically acceptable basic addition salt" is any non-toxic organic or inorganic base addition salt of the acid compounds represented by Formulae I and VI or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality elsewhere in the molecule is not hydrolyzed. The selection criteria for the appropriate salt will be known to one skilled in the art.

"Solvate" means a compound of Formula I or II or the pharmaceutically acceptable salt of a compound of Formula I or II wherein molecules of a suitable solvent are incorporated in a crystal lattice. A suitable solvent is physiologically tolerable at the dosage administered as the solvate. Examples of suitable solvents are ethanol and the like.

The term "stereoisomers" is a general term for all isomers of the individual molecules that differ only in the orientation of their atoms in space. It includes image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The present invention includes within its scope prodrugs of the compounds of Formulae I and VI. In general, such prodrugs will be functional derivatives of the compounds of Formula I or VI which are readily convertible in vivo into the required compound of Formula I or VI. Conventional procedures for the selection and preparation of suitable prodrug derivatives are described, for example, in "Design of Prodrugs" ed. H. Bundgaard, Elsevier, 1985.

DETAILED DESCRIPTION AND PREFERRED EMBODIMENTS

Suitable values for $R^1$ are H, alkyl and the counter ion for a basic addition salt, in particular H, methyl and sodium. Preferably, $R^1$ is H or sodium.

Suitable values for $R^2$, $R^3$, $R^4$, $R^9$ and $R^{10}$ are H and alkyl, in particular H and methyl. Preferably $R^2$, $R^3$, $R^4$, $R^9$ and $R^{10}$ are all H.

Suitable values for $R^5$ and $R^6$ are H, alkyl and phenyl, particularly H, methyl and phenyl. In a preferred embodiment, one of $R^5$ and $R^6$ is H and the other is methyl.

Suitably, $R^5$ and $R^6$ may together form a methylene group or may together form a spirocyclic ring.

The values for X are suitably selected from the group consisting of $CR^9R^{10}$, S, O, SO, $SO_2$, NH and N-alkyl. In specific embodiments, X is selected from O, S, NH and $CH_2$. Preferably X is O.

In a further embodiment of the invention, when X is $CR^9R^{10}$ one of $R^5$ or $R^6$ may form a double bond with one of $R^9$ or $R^{10}$. In yet another embodiment of the invention, both of $R^5$ and $R^6$ may form a triple bond with $R^9$ and $R^{10}$.

The compounds of the invention suitably include those where $R^7$ is selected from one of the groups defined by Formula II, III, IV or V which can be optionally substituted at nodes other than $R^8$ with 1–4 groups selected from alkyl, halo, aryl (which may be substituted as for $R^8$), trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2NH$alkyl, —$SO_2N(alkyl)_2$ and 1,2-methylenedioxy, suitably 1–2 groups selected from methyl, bromo, flouro, chloro or methoxy.

Within the group of Formula Ill, Y is suitably selected from O, S, SO, NH, N-alkyl, $CH_2$, CH-alkyl, $C(alkyl)_2$, and C=O, specifically O, S and $CMe_2$. In preferred embodiments, Y is O.

Within the group of Formula IV, —represents a single or double bond and Z is selected from the group consisting of $CH_2$, O, S, NH and N-alkyl when—is a single bond and Z is selected from the group consisting of CH and N when—is a double bond. In specific embodiments, —is a single bond and Z is CH, or—is a double bond and Z is CH.

Suitable groups for $R^7$ include 9-($R^8$)-9H-fluoren-9-yl, 2-fluoro-9-($R^8$)-9H-fluoren-9-yl, 9-($R^8$)-9H-xanthen-9-yl, 5-($R^8$)-5H-dibenzo[a,d]cyclohepten-5-yl, 9-($R^8$)-9H-thioxanthen-9-yl, 10,10-dimethyl-9-($R^3$)-9,10-dihydroanthracen-9-yl, 10,11-dihydro-5-($R^8$)-5H-dibenzo[a,d]cyclohepten-5-yl, 2,7-dibromo-9-($R^8$)-9H-fluoren-9-yl, 2,7-dichloro-9-($R^8$)-9H-fluoren-9-yl and 8-($R^8$)-8H-indeno[2,1-b]thiophen-8-yl. Preferably, $R^7$ is unsubstituted 9-($R^3$)-9H-fluoren-9-yl or 8-($R^8$)-8H-indeno[2,1-b]thiophen-8-yl.

Within $R^7$, suitable values for $R^8$ are selected from H, alkyl, benzyl, cycloalkyl, indanyl and an optionally substituted aryl group. Suitable aryl groups include thienyl, furanyl, imidazolyl, thiazolyl, phenyl, pyridyl, naphthyl, indolyl, benzothienyl and the like. There may be 1–4 substituents on the aromatic or heteroaromatic ring and these substituents are optionally selected from 1–4 members of the group consisting of alkyl, halo, aryl, trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2NH$alkyl, —$SO_2N(alkyl)_2$ and 1,2-methylenedioxy. More specifically, $R^8$ is selected from H, alkyl, benzyl, cyclohexyl, thienyl, phenyl and naphthyl which are optionally substituted with 1–3 substituents selected from methyl, ethyl, bromo, chloro, fluoro, phenyl, trifluoromethyl and methoxy.

Particular values for $R^8$ include H, phenyl, thien-2-yl, 3-methylphenyl, 4-fluorophenyl, 4-chlorophenyl, 4-methylphenyl, 2-methylphenyl, cyclohexyl, 2,4,6-trimethylphenyl, 2-fluorophenyl, 3,4-methylenedioxyphenyl, 3-methylthien-2-yl, 3-chlorophenyl, 3-methoxyphenyl, butyl, 3,4-dimethoxyphenyl, 5-chlorothien-2-yl, 3-trifluoromethylphenyl, 4-methoxyphenyl, 4-ethylphenyl, 3-ethylphenyl, naphth-2-yl and 3-biphenyl. Preferably, $R^8$ is phenyl and thien-2-yl, both optionally substituted with one substituent selected from methyl, ethyl, methoxy, chloro, fluoro and trifluoromethyl.

In embodiments of the invention, the compounds of Formulae I and VI include:

O-(9-Phenyl-9H-fluoren-9-yl)-L-serine;
O-[9-(2-Thienyl)-9H-fluoren-9-yl]-L-serine;
O-(2-Fluoro-9-phenyl-9H-fluoren-9-yl)-L-serine;
O-(9-Phenyl-9H-fluoren-9-yl)-L-threonine
O-[9-(2-Thienyl)-9H-fluoren-9-yl]-L-threonine;
O-(9-Phenyl-9H-xanthen-9-yl)-L-serine;
O-[9-(3-Methylphenyl)-9H-fluoren-9-yl]-L-serine;
O-[9-(4-Fluorophenyl)-9H-fluoren-9-yl]-L-serine;
O-[9-(4-Fluorophenyl)-9H-fluoren-9-yl]-L-threonine;
O-(9-Phenyl-9H-xanthen-9-yl)-L-threonine;
O-[9-(4-Chlorophenyl)-9H-fluoren-9-yl]-L-serine;
O-[5-(2-Thienyl)-5H-d ibenzo[a,d]cyclohepten-5-yl]-L-serine;
O-[9-(3-Methylphenyl)-9H-xanthen-9-yl]-L-serine;
O-[9-(4-Methylphenyl )-9H-fluoren-9-yl]-L-serine;
O-[9-(2-Methylthien-5-yl )-9H-fluoren-9-yl]-L-serine;
O-(9-Phenyl-9H-thioxanthen-9-yl)-L-serine;
O-[9-(3-Methylphenyl)-9H-xanthen-9-yl]-L-threonine;
O-(10,10-Dimethyl-9-phenyl-9,10-dihydroanthracen-9-yl)-L-serine;
O-[9-(3-Methylphenyl )-9H-thioxanthen-9-yl]-L-serine;
O-[9-(4-Chlorophenyl)-9H-fluoren-9-yl]-L-threonine;
O-(2,7-Dichloro-9-phenyl-9H-fluoren-9-yl)-L-serine;
β-(9-Phenyl-9H-fluoren-9-yl)oxy-DL-β-hydroxynorvaline;
O-(9-Phenyl-9H-fluoren-9-yl)-L-allothreonine;
O-[9-(4-Fluorophenyl)-9H-xanthen-9-yl]-L-threonine;
O-(10,11-Dihydro-5-phenyl-5H-dibenzo[a,d]cyclohepten-5-yl)-L-serine;
O-(5-Phenyl-5H-dibenzo[a,d]cyclohepten-5-yl)-L-serine;
O-[9-(4-Methylphenyl)-9H-thioxanthen-9-yl]-L-serine;
O-[9-(4-Methyl phenyl)-9H-xanthen-9-yl]-L-serine;
O-(9-Phenyl-9H-fluoren-9-yl)-DL-threo-3-phenylserine;
O-[9-(4-Fluorophenyl)-9H-xanthen-9-yl]-L-serine;
O-[10,11-Dihydro-5-(2-thienyl)-5H-dibenzo[a,d]cyclohepten-5-y]-L-serine;
O-(9-Cyclohexyl-9H-fluoren-9-yl)-L-serine;
O-(9-Phenyl-9H-xanthen-9-yl)-D-threonine;
O-[5-(3-Methylphenyl)-5H-dibenzo[a,d]cyclohepten-5-yl]-L-serine;
O-[5-(4-Methylphenyl)-5H-dibenzo[a,d]cyclohepten-5-yl]-L-serine;
O-(9-Phenyl-9H-xanthen-9-yl)-D-serine;
O-[9-(4-Methylphenyl)-9H-xanthen-9-yl]-D-serine;
O-[9-(3-Methylphenyl)-9H-xanthen-9-yl]-D-serine;
O-(9-Phenyl-9H-fluoren-9-yl)-D-serine;
O-(2,7-Dibromo-9-phenyl-9H-fluoren-9-yl)-L-serine;
O-[9-(2,4,6-Trimethylphenyl)-9H-fluoren-9-yl]-L-serine;
O-[9-Phenylmethyl-9H-fluoren-9-yl]-L-serine;

O-[9-(2-Fluorophenyl)-9H-fluoren-9-yl]-L-threonine;
O-[9-(3,4-Methylenedioxyphenyl)-9H-fluoren-9-yl]-L-threonine;
O-[9-(3-Chlorophenyl)-9H-fluoren-9-yl]-L-threonine;
O-[9-(3-Methoxyphenyl)-9H-fluoren-9-yl]-L-threonine;
O-[9-(2-Methylphenyl)-9H-fluoren-9-yl]-L-threonine;
O-(9-Butyl-9H-fluoren-9-yl)-L-threonine;
O-[9-(3,4-Dimethoxyphenyl)-9H-fluoren-9-yl]-L-threonine;
O-[9-(3-Methylthien-2-yl)-9H-fluoren-9-yl]-L-threonine;
O-[9-(2-Methoxyphenyl)-9H-fluoren-9-yl]-L-threonine;
O-[9-(5-Chlorothien-2-yl)-9H-fluoren-9-yl]-L-threonine;
O-[9-(3-Trifluoromethylphenyl)-9H-fluoren-9-yl]-L-threonine;
O-[9-(4-Methoxyphenyl)-9H-fluoren-9-yl]-L-threonine;
O-[9-(4-Ethylphenyl)-9H-fluoren-9-yl]-L-threonine;
O-[9-(3-Ethylphenyl)-9H-fluoren-9-yl]-L-threonine;
O-[9-(2-Naphthyl)-9H-fluoren-9-yl]-L-threonine;
O-[9-(3-Biphenyl)-9H-fluoren-9-yl]-L-threonine;
N-Methyl-O-(9-phenyl-9H-fluoren-9-yl)-L-serine;
N,N-Dimethyl-O-(9-phenyl-9H-fluoren-9-yl)-L-serine;
S-(9-Phenyl-9H-thioxanthen-9-yl)-D,L-cysteine;
S-[9-(3-Methylphenyl )-9H-thioxanthen-9-yl]-DL-cysteine;
S-[9-(4-Methylphenyl)-9H-thioxanthen-9-yl]-D,L-cysteine;
S-(5-Phenyl-5H-dibenzo[a,d]cyclohepten-5-yl)-D,L-cysteine;
S-[5-(3-Methylphenyl)-5H-dibenzo[a,d]cyclohepten-5-yl]-D,L-cysteine;
S-[5-(4-Methylphenyl)-5H-dibenzo[a,d]cyclohepten-5-yl]-D,L-cysteine;
S-(10,11-Dihydro-5-phenyl-5H-dibenzo[a,d]cyclohepten-5-yl)-D,L-cysteine;
S-[9-(3-Methylphenyl)-9H-fluoren-9-yl]-D,L-cysteine;
S-[9-(4-Methylphenyl)-9H-fluoren-9-yl]-D,L-cysteine;
S-(10,10-Dimethyl-9-phenyl-9,10-dihydroanthracen-9-yl)-D,L-cysteine;
S-(7-Phenyl-7H-benz[d,e]anthracen-7-yl )-D,L-cysteine;
S-(2,7-Dibromo-9-phenyl-9H-fluoren-9-yl)-D,L-cysteine;
S-(9-Phenyl-9H-fluoren-9-yl)-D,L-cysteine;
$N^\alpha$-(9-Phenyl-9H-fluoren-9-yl)-DL-$\alpha,\beta$-diaminopropionic acid;
4-(9-Phenyl-9H-fluoren-9-yl)-DL-2-aminobutyric acid;
O-(10,11-Dihydro-5H-dibenzo[a,d]cyclohepten-5-yl)-L-serine;
O-(9H-fluoren-9-yl)-L-serine; and
O-(9-t-butyl-9H-fluoren-9-yl)-L-serine.

In specific embodiments of the invention, the compounds of Formulae I and VI include:
O-(9-Phenyl-9H-fluoren-9-yl)-L-serine;
O-[9-(2-Thienyl)-9H-fluoren-9-yl]-L-serine;
O-(2-Fluoro-9-phenyl-9H-fluoren-9-yl)-L-serine;
O-(9-Phenyl-9H-fluoren-9-yl)-L-threonine
O-[9-(2-Thienyl)-9H-fluoren-9-yl]-L-threonine;
O-(9-Phenyl-9H-xanthen-9-yl)-L-serine;
O-[9-(3-Methylphenyl)-9H-fluoren-9-yl]-L-serine;
O-[9-(4-Fluorophenyl)-9H-fluoren-9-yl]-L-serine;
O-[9-(4-Fluorophenyl)-9H-fluoren-9-yl]-L-threonine;
O-(9-Phenyl-9H-xanthen-9-yl)-L-threonine;
O-[9-(4-Chlorophenyl)-9H-fluoren-9-yl]-L-serine;
O-[5-(2-Thienyl)-5H-dibenzo[a,d]cyclohepten-5-yl]-L-serine;
O-[9-(3-Methylphenyl)-9H-xanthen-9-yl]-L-serine;
O-[9-(4-Methylphenyl)-9H-fluoren-9-yl]-L-serine;
O-[9-(2-Methylthien-5-yl )-9H-fluoren-9-yl]-L-serine;
O-(9-Phenyl-9H-thioxanthen-9-yl)-L-serine;
O-[9-(3-Methylphenyl)-9H-xanthen-9-yl]-L-threonine;
O-(10,10-Dimethyl-9-phenyl-9,10-dihydroanthracen-9-yl)-L-serine;
O-[9-(3-Methylphenyl)-9H-thioxanthen-9-yl]-L-serine;
O-[9-(4-Chlorophenyl)-9H-fluoren-9-yl]-L-threonine;
O-(2,7-Dichloro-9-phenyl-9H-fluoren-9-yl)-L-serine;
$\beta$-(9-Phenyl-9H-fluoren-9-yl)oxy-DL-p-hydroxynorvaline;
O-(9-Phenyl-9H-fluoren-9-yl)-L-allothreonine;
O-[9-(4-Fluorophenyl)-9H-xanthen-9-yl]-L-threonine;
O-(10,11-Dihydro-5-phenyl-5H-dibenzo[a,d]cyclohepten-5-yl)-L-serine;
O-(5-Phenyl-5H-dibenzo[a,d]cyclohepten-5-yl)-L-serine;
O-[9-(4-Methylphenyl)-9H-thioxanthen-9-yl]-L-serine;
O-[9-(4-Methylphenyl)-9H-xanthen-9-yl]-L-serine;
O-(9-Phenyl-9H-fluoren-9-yl)-DL-threo-3-phenylserine;
O-[9-(4-Fluorophenyl)-9H-xanthen-9-yl]-L-serine;
O-[10,11-Dihydro-5-(2-thienyl)-5H-dibenzo[a,d]cyclohepten-5-yl]-L-serine;
O-[9-(2-Fluorophenyl)-9H-fluoren-9-yl]-L-threonine;
O-[9-(3-Chlorophenyl)-9H-fluoren-9-yl]-L-threonine;
O-[9-(3-Methoxyphenyl)-9H-fluoren-9-yl]-L-threonine;
O-[9-(2-Methylphenyl)-9H-fluoren-9-yl]-L-threonine;
O-[9-(3-Methylthien-2-yl)-9H-fluoren-9-yl]-L-threonine;
O-[9-(2-Methoxyphenyl)-9H-fluoren-9-yl]-L-threonine;
O-[9-(5-Chorothien-2-yl)-9H-fluoren-9-yl]-L-threonine;
O-[9-(3-Trifluoromethylphenyl)-9H-fluoren-9-y i]-L-threonine;
O-[9-(4-Methoxyphenyl)-9H-fluoren-9-yl]-L-threonine;
O-[9-(4-Ethylphenyl)-9H-fluoren-9-yl]-L-threonine;
O-[9-(3-Ethylphenyl)-9H-fluoren-9-yl]-L-threonine;
O-[9-(2-Naphthyl)-9H-fluoren-9-yl]-L-threonine;
O-[9-(3-Biphenyl)-9H-fluoren-9-yl]-L-threonine;
N-Methyl-O-(9-phenyl-9H-fluoren-9-yl)-L-serine;
S-(9-Phenyl-9H-thioxanthen-9-yl)-D,L-cysteine;
S-[9-(3-Methylphenyl)-9H-thioxanthen-9-yl]-DL-cysteine;
S-[9-(4-Methylphenyl )-9H-thioxanthen-9-yl]-D,L-cysteine;
S-(5-Phenyl-5H-dibenzo[a,d]cyclohepten-5-yl)-D,L-cysteine;
S-[5-(3-Methylphenyl)-5H-dibenzo[a,d]cyclohepten-5-yl]-D,L-cysteine;
S-[9-(3-Methylphenyl)-9H-fluoren-9-yl]-D,L-cysteine;
S-(9-Phenyl-9H-fluoren-9-yl)-D,L-cysteine;
S-(7-Phenyl-7H-benz[d, e]anthracen-7-yl )-D,L-cysteine;
$N^\alpha$-(9-Phenyl-9H-fluoren-9-yl)-DL-$\alpha,\beta$-diaminopropionic acid;
4-(9-Phenyl-9H-fluoren-9-yl)-DL-2-aminobutyric acid;
and the sodium salts thereof.

In more specific embodiments of the invention, the compounds of Formulae I and VI include:
O-(9-Phenyl-9H-fluoren-9-yl)-L-serine;
O-[9-(2-Thienyl)-9H-fluoren-9-yl]-L-serine;
O-(2-Fluoro-9-phenyl-9H-fluoren-9-yl)-L-serine;
O-(9-Phenyl-9H-fluoren-9-yl)-L-threonine
O-[9-(2-Thienyl )-9H-fluoren-9-yl]-L-threonine;
O-(9-Phenyl-9H-xanthen-9-yl)-L-serine;
O-[9-(3-Methylphenyl)-9H-fluoren-9-yl]-L-serine;
O-[9-(4-Fluorophenyl)-9H-fluoren-9-yl]-L-serine;
O-[9-(4-Fluorophenyl)-9H-fluoren-9-yl]-L-threonine;
O-(9-Phenyl-9H-xanthen-9-yl)-L-threonine;
O-[9-(4-Chlorophenyl)-9H-fluoren-9-yl]-L-serine;
O-[9-(4-Methylphenyl)-9H-fluoren-9-yl]-L-serine;
O-[9-(2-Methylthien-5-yl)-9H-fluoren-9-yl]-L-serine;
O-(9-Phenyl-9H-thioxanthen-9-yl)-L-serine;
O-[9-(3-Methylphenyl)-9H-xanthen-9-yl]-L-threonine;
O-(10,10-Dimethyl-9-phenyl-9,10-dihydroanthracen-9-yl)-L-serine;
O-[9-(3-Methylphenyl)-9H-thioxanthen-9-yl]-L-serine;
O-(2,7-Dichloro-9-phenyl-9H-fluoren-9-yl)-L-serine;
$\beta$-(9-Phenyl-9H-fluoren-9-yl)oxy-DL-$\beta$-hydroxynorvaline;

O-[9-(4-Fluorophenyl)-9H-xanthen-9-yl]-L-threonine;
O-(5-Phenyl-5H-dibenzo[a,d]cyclohepten-5-yl)-L-serine;
O-[9-(4-Methylphenyl)-9H-thioxanthen-9-yl]-L-serine;
O-[9-(4-Methylphenyl)-9H-xanthen-9-yl]-L-serine;
O-(9-Phenyl-9H-fluoren-9-yl)-DL-threo-3-phenylserine;
O-[10,11-Dihydro-5-(2-thienyl)-5H-dibenzo[a,d]cyclohepten-5-yl]-L-serine;
O-[9-(2-Fluorophenyl)-9H-fluoren-9-yl]-L-threonine;
O-[9-(3-Chlorophenyl)-9H-fluoren-9-yl]-L-threonine;
O-[9-(3-Methoxyphenyl)-9H-fluoren-9-yl]-L-threonine;
O-[9-(2-Methylphenyl)-9H-fluoren-9-yl]-L-threonine;
O-[9-(3-Methylthien-2-yl)-9H-fluoren-9-yl]-L-threonine;
O-[9-(2-Methoxyphenyl)-9H-fluoren-9-yl]-L-threonine;
O-[9-(5-Chlorothien-2-yl)-9H-fluoren-9-yl]-L-threonine;
O-[9-(3-Trifluoromethylphenyl)-9H-fluoren-9-yl]-L-threonine;
O-[9-(4-Methoxyphenyl)-9H-fluoren-9-yl]-L-threonine;
O-[9-(4-Ethylphenyl)-9H-fluoren-9-yl]-L-threonine;
O-[9-(3-Ethylphenyl)-9H-fluoren-9-yl]-L-threonine;
O-[9-(2-Naphthyl)-9H-fluoren-9-yl]-L-threonine;
O-[9-(3-Biphenyl)-9H-fluoren-9-yl]-L-threonine;
S-(9-Phenyl-9H-thioxanthen-9-yl)-D,L-cysteine;
S-[9-(3-Methylphenyl)-9H-thioxanthen-9-yl]-DL-cysteine;
S-[9-(4-Methylphenyl)-9H-thioxanthen-9-yl]-D,L-cysteine;
S-(5-Phenyl-5H-dibenzo[a,d]cyclohepten-5-yl )-D,L-cysteine;
S-[5-(3-Methylphenyl)-5H-dibenzo[a,d]cyclohepten-5-yl]-D,L-cysteine;
S-[9-(3-Methylphenyl)-9H-fluoren-9-yl]-D,L-cysteine;
S-(9-Phenyl-9H-fluoren-9-yl)-D,L-cysteine
$N^{\alpha}$-(9-Phenyl-9H-fluoren-9-yl)-DL-$\alpha,\beta$-diaminopropionic acid;
4-(9-Phenyl-9H-fluoren-9-yl)-DL-2-aminobutyric acid;
and the sodium salts thereof.

In even more specific embodiments of the invention, the compounds of Formulae I and VI include:
O-(9-Phenyl-9H-fluoren-9-yl)-L-threonine
O-[9-(2-Thienyl)-9H-fluoren-9-yl]-L-threonine;
O-(9-Phenyl-9H-xanthen-9-yl)-L-serine;
O-[9-(4-Fluorophenyl)-9H-fluoren-9-yl]-L-threonine;
O-(9-Phenyl-9H-xanthen-9-yl)-L-threonine;
O-[9-(3-Methylphenyl)-9H-xanthen-9-yl]-L-threonine;
?β-(9-Phenyl-9H-fluoren-9-yl)oxy-DL-norvaline;
O-[9-(4-Fluorophenyl)-9H-xanthen-9-yl]-L-threonine;
O-(9-Phenyl-9H-fluoren-9-yl)-DL-threo-3-phenylserine;
O-[9-(2-Fluorophenyl)-9H-fluoren-9-yl]-L-threonine;
O-[9-(3-Chlorophenyl)-9H-fluoren-9-yl]-L-threonine;
O-[9-(3-Methoxyphenyl)-9H-fluoren-9-yl]-L-threonine;
O-[9-(2-Methylphenyl)-9H-fluoren-9-yl]-L-threonine;
O-[9-(3-Methylthien-2-yl)-9H-fluoren-9-yl]-L-threonine;
O-[9-(2-Methoxyphenyl)-9H-fluoren-9-yl]-L-threonine;
O-[9-(5-Chlorothien-2-yl)-9H-fluoren-9-yl]-L-threonine;
O-[9-(3-Trifluoromethylphenyl)-9H-fluoren-9-yl]-L-threonine;
O-[9-(4-Ethylphenyl)-9H-fluoren-9-yl]-L-threonine;
S-[9-(3-Methylphenyl)-9H-thioxanthen-9-yl]-DL-cysteine;
S-[9-(4-Methylphenyl)-9H-thioxanthen-9-yl]-D,L-cysteine;
S-(5-Phenyl-5H-dibenzo[a,d]cyclohepten-5-yl)-D,L-cysteine;
O-(8-Phenyl-8H-indeno[2,1-b]thiophen-8-yl)-L-threonine
O-(8-Phenyl-8H-indeno[2,1-b]thiophen-8-yl)-L-serine
O-[9-(2-Biphenyl)-9H-fluoren-9-yl]-L-serine;
O-[9-(2-Biphenyl)-9H-fluoren-9-yl]-L-threonine;
O-[9-Phenyl-9H-fluoren-9-yl]-D,L-α-methylserine;
O-{9-[3-(4-Fluorophenyl)thien-2-yl]-9H-fluoren-9-yl}-L-threonine;
O-{9-[3-(4-Methoxyphenyl)thien-2-yl]-9H-fluoren-9-yl}-L-threonine;
O-[9-(Benzo[b]thien-2-yl)-9H-fluoren-9-yl]-L-threonine;
O-[(5-Indolyl)-9H-fluoren-9-yl]-L-threonine;
O-(8-Phenyl-8H-indeno[2,1-b]thiophen-8-yl)-L-threonine;
O-(8-Phenyl-8H-indeno[2,1-b]thiophen-8-yl)-L-serine;
O-(1-Phenyl-9H-fluoren-9-yl)-L-serine;
O-(Benzo[b]indeno[1,2-d]thiophen-6-yl)-L-serine;
and the sodium salts thereof.

In the most specific embodiments of the invention, the compounds of Formulae I and VI include:
O-(9-Phenyl-9H-fluoren-9-yl)-L-threonine
O-[9-(2-Thienyl)-9H-fluoren-9-yl]-L-threonine;
O-[9-(3-Chlorophenyl)-9H-fluoren-9-yl]-L-threonine;
O-[9-(3-Methoxyphenyl)-9H-fluoren-9-yl]-L-threonine;
O-[9-(2-Methylphenyl)-9H-fluoren-9-yl]-L-threonine;
O-[9-(3-Methylthien-2-yl )-9H-fluoren-9-yl]-L-threonine;
and the sodium salts thereof.

Compounds of Formulae I and VI can be considered to be amino acids or derivatives thereof. Compounds which contain, instead of a carboxylate group, a "carboxylate equivalent" group, such as hydroxamic acids, phosphonic acids, phosphinic acids, sulfonic acids, sulfinic acids, amides or tetrazoles are also considered embodiments of the present invention.

In another embodiment of the invention, a compound of Formulae I or VI is provided in labeled form, such as radiolabeled form, e.g. labeled by incorporation within its structure $^{3}$H or $^{14}$C or by conjugation to 125I. In a preferred aspect of the invention, those compounds of the invention which bind preferentially to GlyT-2 versus GlyT-1 can be used, in labeled form, to identify GlyT-2 receptor ligands by techniques common in the art. This can be achieved by incubating the receptor or tissue in the presence of a ligand candidate and then incubating the resulting preparation with an equimolar amount of radiolabeled compound of the invention. GlyT-2 receptor ligands are thus revealed as those that significantly occupy the GlyT-2 site and prevent binding of the radiolabeled compound of the present invention. Alternatively, GlyT-2 receptor ligand candidates may be identified by first incubating a radiolabeled form of a compound of the invention then incubating the resulting preparation in the presence of the candidate ligand. A more potent GlyT-2 receptor ligand will, at equimolar concentration, displace the radiolabeled compound of the invention.

Further uses of the radiolabeled compound of the invention include identification of allosteric modulators of GlyT-2 and measuring the rate constants ($k_{on}$ and $k_{off}$) of ligands that bind to GlyT-2. Allosteric modulators will be identified as compounds that inhibit GlyT-2 function (i.e. inhibit glycine transport) but do not displace the radiolabeled compound of the present invention. The on and off rate constants of the radiolabeled compound of the invention can be assessed by incubating the radiolabeled compound with tissues or cells expressing the transporter and then diluting the mix such that the concentration of radiolabeled compound is reduced below its equilibrium dissociation constant (Kd). The rate of association and dissociation can then be calculated by techniques common in the art. The rate constants of GlyT-2 transporter ligand candidates may also be assessed by measuring the rate at which the ligands displace the radiolabeled compound of interest. Finally, the radiolabeled compound of interest will be useful for tissues that express GlyT-2 by either standard membrane binding techniques or autoradiography. These techniques can also be used to identify pathophysiological conditions that result in a change in expression level of GlyT-2.

Acid addition salts of the compounds of Formula I and VI are most suitably formed from pharmaceutically acceptable acids, and include, for example, those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I and VI for laboratory use, or for subsequent conversion to a pharmaceutically acceptable acid addition salt. Also included within the scope of the invention are solvates and hydrates of the invention.

Basic addition salts of the compounds of Formula I and VI are most suitably formed from pharmaceutically acceptable bases and include, for example, those formed with inorganic bases, e.g. sodium, potassium, calcium, magnesium or barium hydroxides, or aliphatic, alicyclic or aromatic organic amines such as methylamine, trimethyl amine and picoline or ammonia. The selection of the appropriate salt may be important so that the ester is not hydrolyzed. The selection criteria for the appropriate salt will be known to one skilled in the art.

The conversion of a given compound salt to a desired compound salt is achieved by applying standard techniques, in which an aqueous solution of the given salt is treated with a solution of base, e.g. sodium carbonate or potassium hydroxide, until the desired pH is reached to liberate the free base but not deprotonate the carboxylic acid if present. The free base is then extracted into an appropriate solvent, such as ether, and then separated from the aqueous portion, dried, and treated with the requisite acid to give the desired acid addition salt. Alternatively, an aqueous solution of the basic addition given salt is treated with a solution of acid, e.g. hydrochloric acid or sulfuric acid, until the desired pH is reached to liberate the free base but not protonate the amine. The free base is then extracted into an appropriate solvent, such as ether, and then separated from the aqueous portion, dried, and treated with the requisite base to give the desired basic addition salt.

All of the compounds of the present invention have at least one chiral center. The invention extends to cover all structural and optical isomers of the various compounds, as well as racemic mixtures thereof.

In accordance with other aspects of the invention, the compounds of the present invention can be prepared by processes analogous to those established in the art. For example, when X=O, compounds of Formulae I and VI may be prepared as shown in Scheme 1. Condensation of appropriately aryl-substituted carbinols A, wherein $R^7$ is as defined in Formulae I and VI, with a serine derivative of Formula B, wherein $R^4$, $R^5$ and $R^6$ are as defined in Formula I and VI, $R^1$ is alkyl and one of $R^2$ and $R^3$ is selected from H and alkyl and the other is $PG^1$, wherein PG is any protecting group which is acid stable (for example the 9-fluorenylmethoxycarbonyl or Fmoc protecting group), in the presence of an acid in an aprotic solvent and optionally under standard conditions for affecting the azeotropic removal of water (e.g. Dean Stark apparatus or molecular sieves). Suitable acids include sulfuric acid, trifluoroacetic acid, p-toluenesulfonic acid, camphor sulfonic acid or various Lewis acids such as $BF_3OEt_2$, with p-toluenesulfonic acid being preferred. Suitable aprotic solvents include toluene, benzene, methylene chloride, chloroform and 1,2-dichloroethane, with toluene being preferred. This reaction can be carried out at a temperature in the range of 0–120° C., preferably 20–120° C. Removal of the nitrogen protecting group ($PG_1$) can be performed using standard deprotection conditions to provide compounds of Formulae I and VI wherein $R^4$–$R^7$ are as defined above, $R^1$ is alkyl and one of $R^2$ and $R^1$ is selected from H and alkyl and the other is H (Formula C below). For example, removal of the Fmoc protecting group may be achieved using piperidine either neat or in an inert solvent such as DMF, toluene, benzene or methylene chloride at temperatures in the range of 0 to 100° C. Preferred conditions are neat piperidine at about room temperature. When compounds of Formula C are treated with inorganic bases, for example sodium hydroxide or lithium hydroxide in a polar solvent such as methanol or ethanol (with methanol being preferred), followed by acidification to a pH of around 4–5 using a standard mineral acid such as hydrochloric acid, compounds of Formulae I and VI wherein $R^4$–$R^7$ are as defined above, $R^1$ is H and one of $R^2$ and $R^3$ is selected from H and alkyl and the other is H (Formula D below) are obtained.

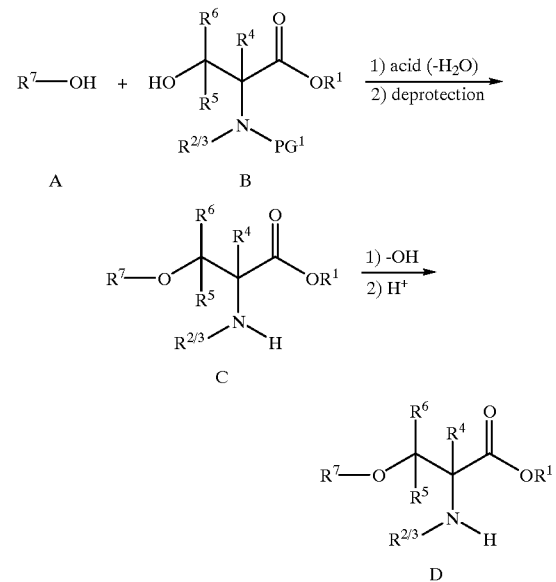

Compounds of Formulae I and VI, wherein X is O, NH or N-alkyl, may be prepared using the method shown in Scheme 2. A compound of Formula E, wherein $R^7$ is as defined in Formulae I and VI and Y is an appropriate leaving group such as chloro, bromo, iodo or mesylate, preferably bromo, is reacted with a amino acid derivative of Formula F, wherein X is selected from O, NH or N-alkyl, $R^1$ is alkyl, one of $R^2$ and $R^3$ is selected from H and alkyl and the other is $PG^2$, wherein $PG^2$ is an appropriate protecting group such as t-BOC, and $R^4$–$R^6$ are as defined in Formulae I and VI, under standard alkylating conditions, for example sodium bicarbonate, potassium carbonate or trialkylamine, in an inert solvent such as acetone or acetonitrile at temperatures in the range of 0 to 100° C. Preferred conditions are potassium carbonate in acetonitrile at room temperature. When the leaving group, Y, is a halide, the reaction may be conducted in the presence of an iodide salt such as potassium iodide. Removal of the protecting group ($PG^2$) can be performed under standard conditions to provide compounds of Formulae I and VI wherein $R^1$, $R^4$–$R^7$ are as defined above and one of $R^2$ and $R^3$ is selected from H and alkyl and the other is H (Formula G below). Hydrolysis of the ester function can be performed as described above to provide compounds of Formulae I and VI wherein $R^1$ is H.

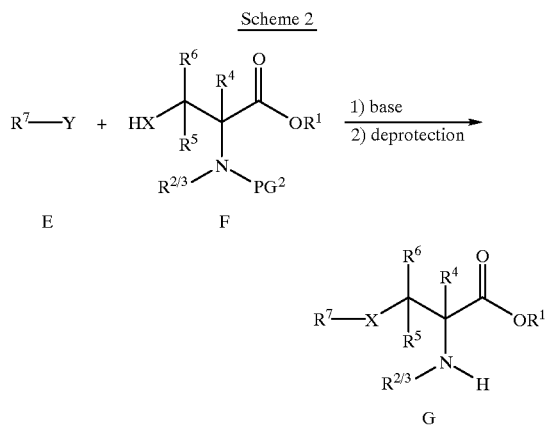

Compounds of Formulae I and VI wherein X is S are readily prepared utilizing the method shown in Scheme 3. An alcohol of Formula A, wherein $R^7$ is as defined in Formulae I and VI, is condensed with cysteine or cysteine derivative of Formula H, wherein $R^1$–$R^6$ are as defined in Formulae I and VI, in the presence of an acid either neat or in an inert solvent and at temperatures in the range of 0–50° C., to provide compounds of Formula J where $R^1$–$R^7$ are as defined in Formulae I and VI. Suitable acids include trifluoroacetic acid, p-toluenesulfonic acid, camphorsulfonic acid and the like and suitable solvents include methylene chloride, chloroform, toluene and the like. Preferred reaction conditions are neat trifluoroacetic acid at room temperature. When $R^1$ is alkyl, the ester functionality of the compounds of Formula J may be hydrolysed as described above to provide compounds of Formulae I and VI wherein $R^1$ is H. Compounds of Formula J can be oxidised under standard conditions, for example either 1 or 2 equivalents of m-chloroperbenzoic acid in methylene chloride, to provide compounds of Formula I and VI wherein X is SO and $SO_2$ respectively.

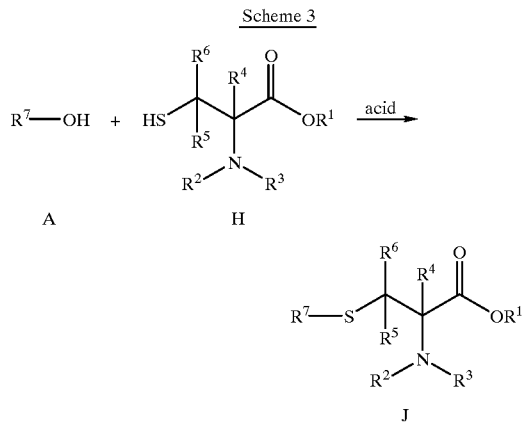

Compounds of Formulae I and VI are also conveniently prepared from the corresponding α-aminonitriles or hydantoin compounds. These methods, described below, are particularly amenable to the preparation of compounds of Formulae I and VI wherein X is O, S or $CH_2$. As shown in Scheme 4, a-aminonitriles K, wherein $R^2$–$R^7$ are as defined in Formula I and VI, may be hydrolysed to the desired free α-amino acid L, wherein $R^2$–$R^7$ are as defined in Formula I and VI, by any well known hydrolysis reaction for nitriles, for example, with a base (preferably a hydroxide, e.g. sodium hydroxide) in the presence of water at elevated temperatures (preferably at or near the reflux temperature of the mixture). Compounds of Formula L may be esterified using standard esterification methods (e.g. $SOCl_2$ and an alkanol) to provide compounds of Formula I and VI wherein $R^1$ is alkyl, or these compounds may be isolated directly from the hydrolysis of the nitrile by substituting an alkanol for water as the solvent.

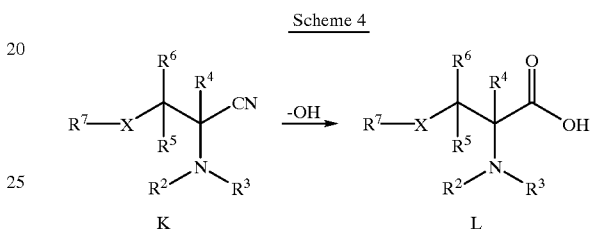

As shown in Scheme 5, hydrolysis of hydantoin compounds M, wherein $R^2$–$R^7$ are as defined in Formula I and VI, using well known methods provides the corresponding amino acids N (compounds of Formulae I and VI wherein one of $R^2$ and $R^3$ is H and the other is selected from H and alkyl, $R^1$ is H and $R^4$–$R^7$ are as defined above). This hydrolysis is effected, for example, by treatment of compounds of Formula M with most alkali or alkaline earth hydroxides (preferably sodium hydroxide). Compounds of Formula N may be esterified using standard esterification methods (e.g. $SOCl_2$ and an alkanol) to provide compounds of Formula I and VI wherein $R^1$ is alkyl.

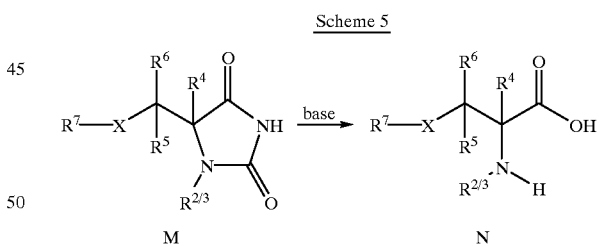

The α-aminonitriles K or hydantoins M are both conveniently prepared from the corresponding aldehydes or ketones of Formula P, wherein X is selected from $CH_2$, S and O and $R^4$–$R^7$ are as defined in Formulae I and VI, as shown in Scheme 6. The nitriles are available by reaction of compounds of Formula P under well-known Strecker conditions, such as reaction with a mixture of sodium or potassium cyanide and ammonia, alkylamines (ethylamine, butylamine and the like), di-alkylamines (dimethylamine, ethylpropylamine and the like), phenylamine or phenyl alkylamines (phenethylamine, phenylmethylamine and the like) at any suitable temperature, preferably at or near room temperature. Hydantoins M are prepared using any well known method for converting compounds of Formula P to a hydantoin, for example, reaction in an inert solvent, such as an alkanol, with a mixture of an alkali cyanide and ammonium carbonate at elevated temperatures and optionally in a sealed tube. Preferred conditions are potassium cyanide and ammonium carbonate in aqueous ethanol in a sealed tube at a temperature in the range of 20–120° C. (preferably 50–120° C.).

When X is S or O, compounds of Formula P may be prepared as shown below in Scheme 7. Reagents Q, wherein $R^7$ is as defined in Formulae I and VI, and X is S or O, are reacted either with reagents R (when $R^4$ is H) or reagents S, (when $R^4$ is alkyl), wherein $R^5$ and $R^6$ are as defined in Formulae I and VI, Y is an appropriate leaving group such as chloro, bromo, iodo or mesylate, preferably bromo, and $PG^3$ may be for example, methyl or together form a cyclic acetal which provides suitable protection for the aldehyde functionality. Conditions suitable to affect the transformation of Q to P include treating reagents Q with sodium in a lower alkanol followed by addition of reagents R or S at temperatures in the range of −80° C. to room temperature. Deprotection of the resulting intermediates may be performed in the presence of acid in an inert solvent at a temperature in the range of 20–100° C. During this latter reaction, care must be taken so as not to hydrolyse the "$R^7$-X-" functionality. When X is O, compounds of Formula P are also available, as shown in Scheme 7, from by the addition of reagents Q, wherein $R^7$ is as defined in Formulae I and VI, to reagents T, wherein $R^4$-$R^6$ are as defined in Formulae I and VI and $PG^4$ is a suitable protecting group such as tetrahydropyranyl or methoxymethyl, using the same conditions described above for the addition and deprotection of reagents Q and R (or S). Oxidation of the resulting alcohol under standard conditions, such as Swern oxidation (oxalyl chloride, DMSO, triethylamine), in an inert solvent such as dichloromethane provides compounds of Formula P, wherein $R^4$-$R^7$ are as defined in Formulae I and VI.

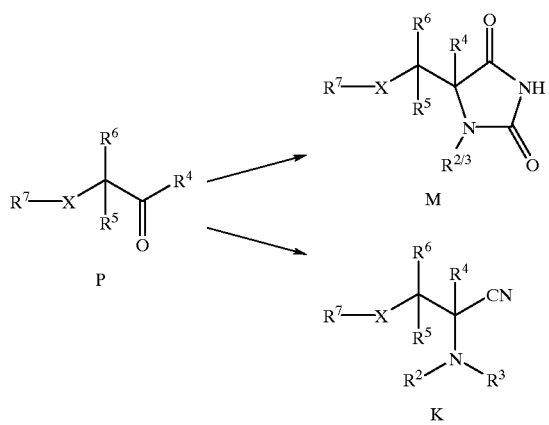

Scheme 6

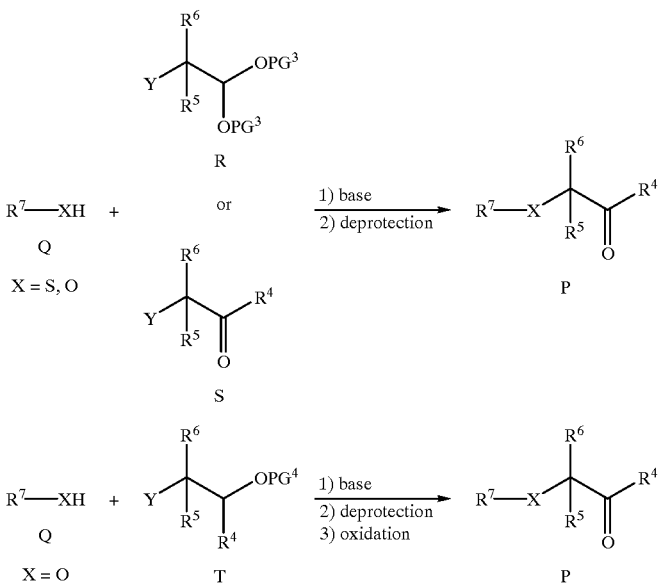

Scheme 7

When X is $CH_2$, compounds of Formula P are available using the methods depicted in Scheme 8. In the first instance, reagents U, wherein $R^7$ is as defined in Formulae I and VI, is treated with a strong base such as an alkyl lithium, in an inert solvent such as tetrahydrofuran or hexanes, at temperatures in the range of −80 to 20° C., followed by the addition of either reagents V (when $R^4$ is H) or reagents W, (when $R^4$ is alkyl), wherein X is $CH_2$, $R^4$–$R^6$ are as defined in Formulae I and VI, Y is an appropriate leaving group, such as halo or tosylate and $PG^3$ is as defined in Formula R. Preferred reaction conditions are n-butyllithium in hexanes at 0° C. Deprotection of the resulting intermediate in the presence of acid in an inert solvent at a temperature in the range of 20–100° C., preferably p-toluenesulfonic acid in acetone at a refluxing temperature, provides compounds of Formula P, wherein X is $CH_2$ and $R^4$–$R^7$ are as defined in Formulae I and VI. Alternatively, reagents U, wherein $R^7$ is as defined in Formulae I and VI, are treated with a strong base such as an alkyl lithium, in an inert solvent such as tetrahydrofuran or hexanes, at temperatures in the range of −80 to 20° C., followed by the addition of reagents Z, wherein Y is an appropriate leaving group, such as halo or tosylate, X is $CH_2$ and $PG^4$ is as defined in Formula T, followed by deprotection in the presence of a suitable acid (e.g. HCl) and oxidation using standard conditions (for example Swern oxidation) to provide compounds of Formula P, wherein X is $CH_2$ and $R^4$–$R^7$ are as defined in Formulae I and VI.

Various alkyl amine derivatives of the compounds of Formulae I and VI are readily formed by the reaction of primary or secondary amines of, for example, compounds of Formulae D, G and J, with compounds of Formula $R^{2/3}$—Y, wherein Y is an appropriate leaving group and $R^{2/3}$ is alkyl, under standard alkylation conditions. Primary amines of compounds of Formulae D, G and J may also be treated under standard reductive alkylation conditions with aldehydes of Formula $R^{2/3}$—C(O)H to provide monoalkylated compounds of Formulae I and VI which may be further alkylated under standard conditions with compounds of Formula $R^{2/3}$—Y, to provide the corresponding secondary amines.

Compounds of Formulae B, F and H are well known amino acids and derivatives thereof. These compounds are commercially available in both racemic and enantiomerically pure forms or can be prepared using methods known to one skilled in the art (for example see Carpino, L. A.; Han, G. Y. *J. Am. Chem. Soc.* 92, 1970:5748–5749 and Paquet, A. *Can. J. Chem.* 60, 1982:976).

Reagents R, S, T, U, V and W are all well known alkanols and derivatives thereof which are either commercially available or readily prepared from commercially available materials using methods known to one skilled in the art.

Reagents of Formula A, wherein $R^8$ is not H, are readily available from the addition of appropriately substituted Grignard reagents or alkyl and aryl lithiums, wherein $R^8$ is as defined in Formulae I and VI and Y is, for example, halo, preferably bromo or chloro, to the corresponding ketones under standard conditions as shown in Scheme 9 for compounds of Formulae I and VI wherein $R^1$ is a group of Formula II and $R^8$ is as defined in Formulae I and VI (other than H).

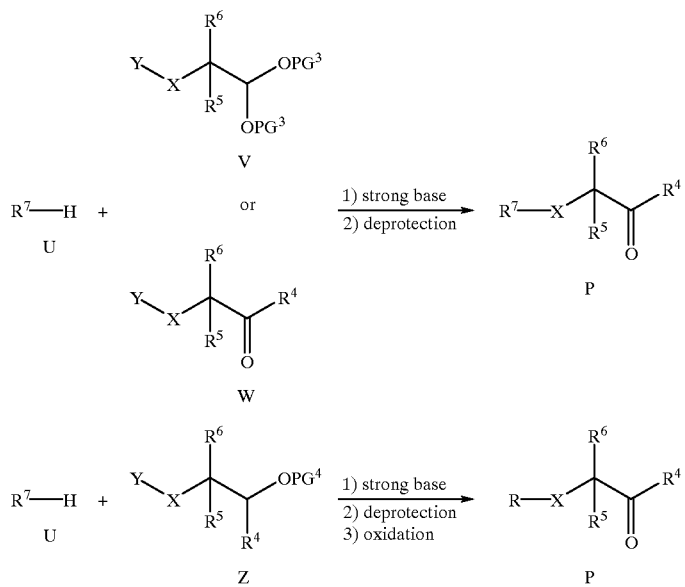

Scheme 8

Scheme 9

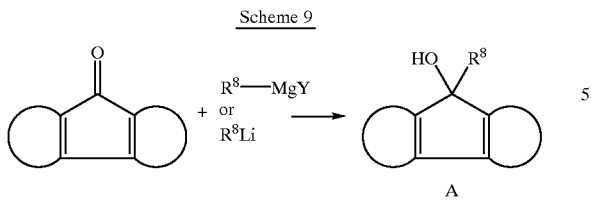

Reagents of Formula A wherein $R^8$ is H are readily available by reduction of the corresponding ketone using any well known reducing agent, for example metal hydrides, such as lithium aluminum hydride, in an inert solvent, such as tetrahydrofuran, and at temperatures in the range of −50–100° C., suitably −20–60° C.

Reagents of Formula A, wherein $R^8$ is as defined in Formulae I and VI, may be converted to reagents of Formula E, T and Q using well known chemistries as shown in Scheme 10 for compounds of Formulae E, T and Q wherein $R^7$ is a group of Formula II. For the preparation of reagents of Formula Q, wherein X is S, compounds of Formula A may be treated with hydrogen sulfide in the presence of an acid or an alkali or alkali earth hydrosulfide (preferably sodium hydrosulfide) in an inert solvent (preferably an alkanol) at elevated temperatures, preferably at or near the reflux temperature of the system. The preparation of reagents of Formula E, wherein Y is an appropriate leaving group, for example halo or tosylate, is readily accomplished using either standard halogenating conditions, for example $CBr_4$/$Ph_3P$ or $SOCl_2$, when Y is bromo or chloro, or via the addition of, for example tosyl or mesyl halide in the presence of a base in an inert solvent, when Y is toslyate or mesylate. It should be understood that Y can be any appropriate leaving group which is available using standard chemistries. Compounds of Formula T may be prepared by the reduction of compounds of Formula A using standard conditions, for example zinc in the presence of an acid as described in Ullmann et al. *Ber.* 73, 904:37.

Scheme 10

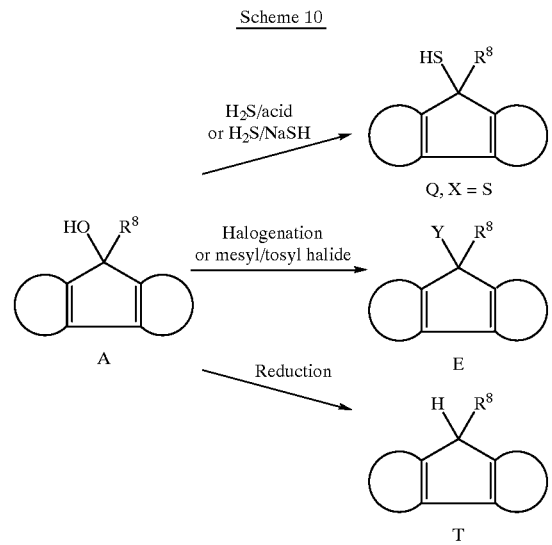

The ketone precursors to compounds of Formula A may be purchased or prepared using standard procedures known to those skilled in the art.

Compounds of Formula I in which one pair of $R^5$ and $R^9$ or $R^6$ and $R^{10}$ together form a double bond may be prepared according to Scheme 11, below. Alcohol U is reduced, for example by catalytic hydrogenation, to give hydrocarbon V which, upon treatment with paraformaldehyde in the presence of a base such as n-butyl lithium gives the methanol derivative W. Oxidation of alcohol W, under Swern conditions, for example, gives aldehyde X which, upon treatment with ylid Y gives intermediate Z which can be transformed into hydantoin AA by treatment with, for example, potassium cyanide. Hydrolysis of this hydantoin under basic conditions gives the product BB.

Scheme 11

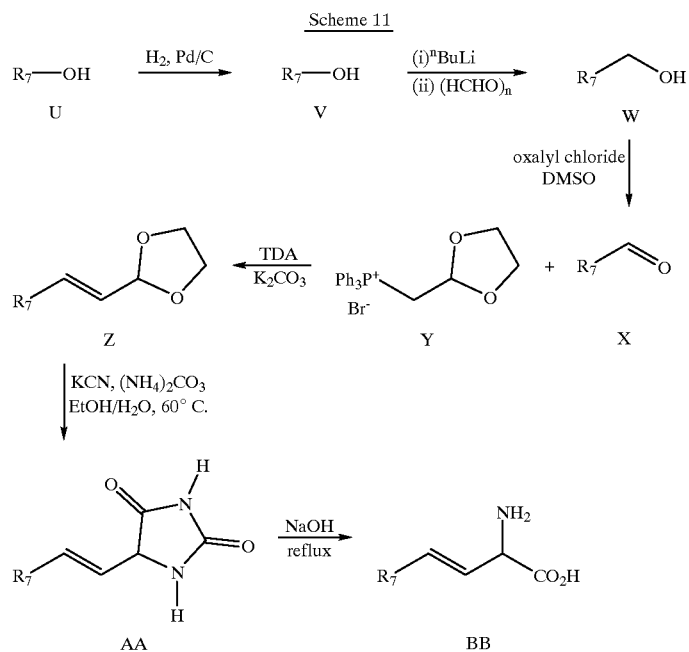

Compounds of Formula I in which both pairs $R^5$ and $R^9$ and $R^6$ and $R^{10}$ together form a triple bond may be prepared according to Scheme 12, below. Acetylene derivative DD is prepared from the corresponding bromide CC by treatment with lithium acetylide-ethylenediamine. Treatment of this acetylene with α-Acetyloxy-N-$^t$Boc-glycine (compound GG, prepared according to the method of Abood et al., Tetrahedron Lett., 1994, 35, 3669–3772) gives intermediate HH, which is deprotected by treatment with HCl in anhydrous ethyl acetate, for example.

-continued

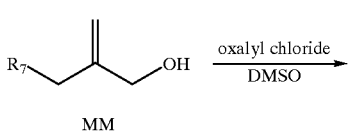

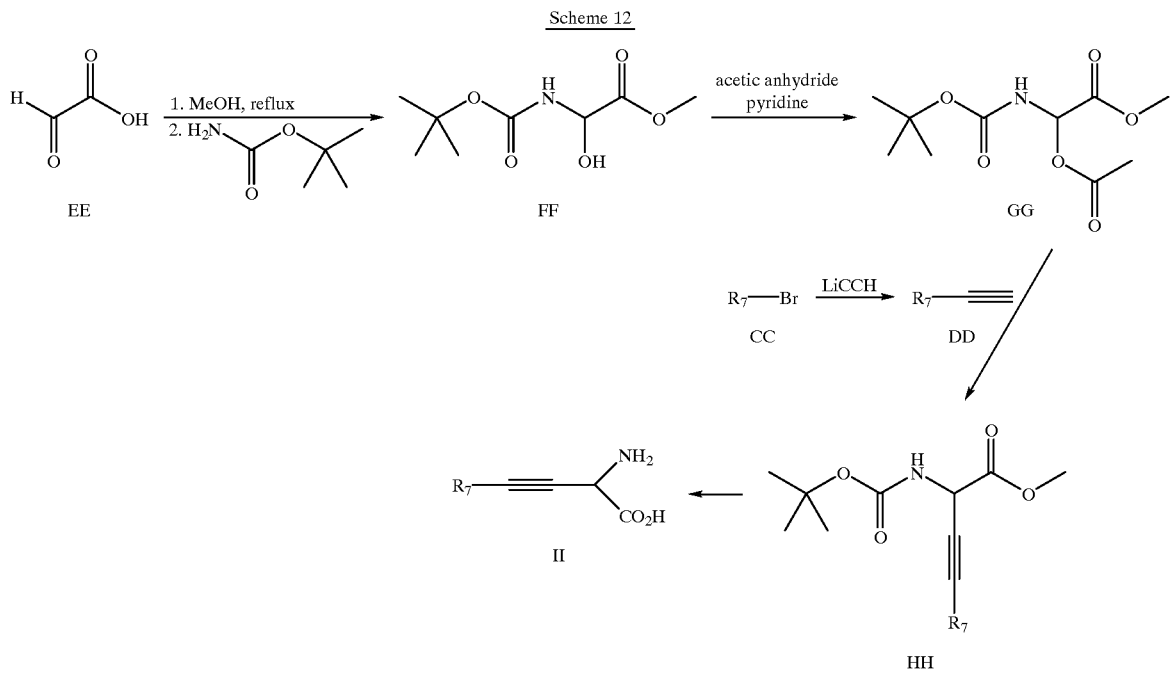

Compounds of Formula I in which $R^5$ and $R^6$ together form a methylene group may be prepared according to Scheme 13, below. Hydrocarbon JJ is functionalised by treatment with dibromopropene in the presence of base, to give bromide KK. Metallation, followed by treatment with carbon dioxide, gives acid LL, which can be reduced to alcohol MM with, for example, borane or di-isobutylaluminium hydride. Oxidation of alcohol MM can be preferentially achieved by treatment with oxalyl chloride. Conversion of the aldehyde NN to amino acid PP can be effected via hydantoin OO, as previously shown in Scheme 11, above.

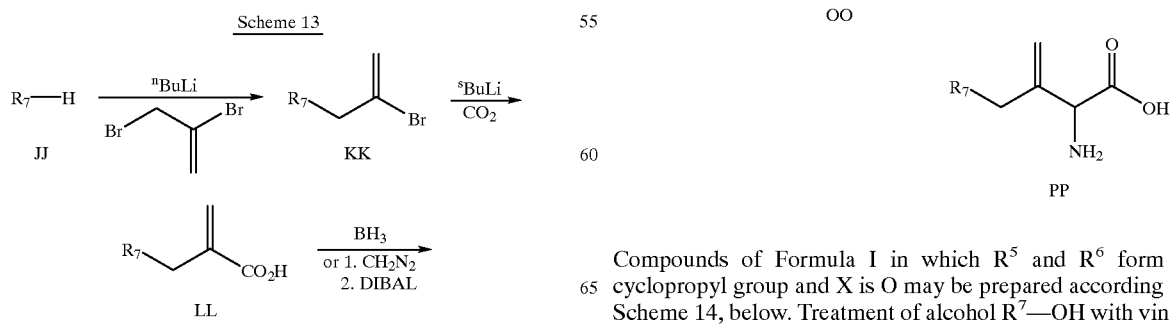

Compounds of Formula I in which $R^5$ and $R^6$ form a cyclopropyl group and X is O may be prepared according to Scheme 14, below. Treatment of alcohol $R^7$—OH with vinyl cyclopropanol RR gives intermediate SS which is converted to aldehyde UU via diol TT. Conversion of the aldehyde to the desired amino acid WW is effected, once more, via hydantoin WW.

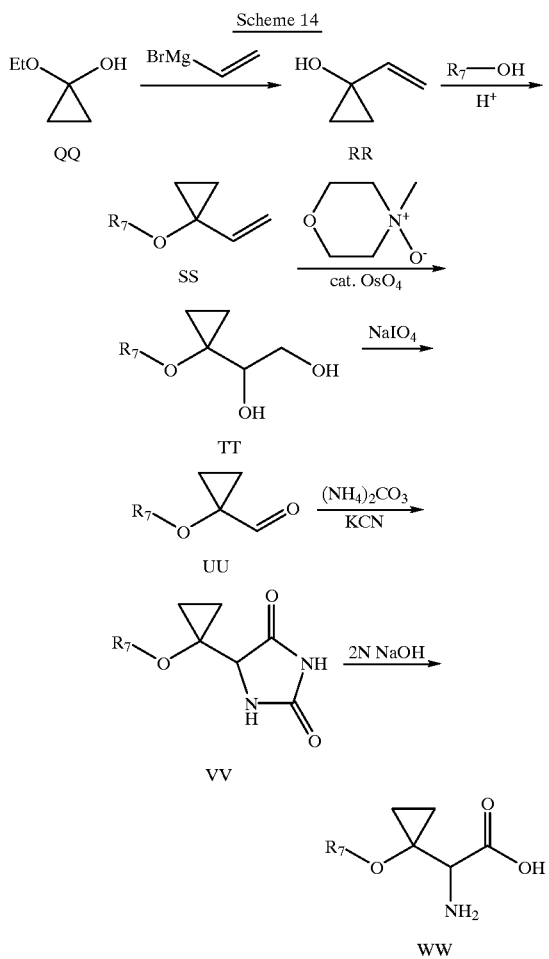

In some cases, the chemistries outlined above may have to be modified, for instance by use of protecting groups, to prevent side reactions due to reactive groups, such as reactive groups attached as substituents.

It should also be noted that the compounds described in the above reaction schemes my be further functionalised to provide other compounds of the invention. For example, compounds wherein $R^2$ and $R^3$ are H can be alkylated using standard techniques well known in the art.

Certain compounds of the invention may also be prepared by adapting the classical solution chemistries outlined above into solid-phase synthetic techniques. For example, $R^1$ can be a residue other than hydrogen representing functionalized resin or suitably selected linker attached to functionalized resin. The linker should be stable under the conditions employed for the above-described reactions. The compounds of the invention where $R^1$ is hydrogen are then cleaved from the resin or the linker leaving the remainder of the molecule intact. For example, solid-phase synthesis of peptoids [oligo(N-substituted glycines)] using a robotic synthesizer was described by Zuckermann et al, *J. Am. Chem. Soc.* 114, 1992:10646–10647 and Spellmeyer et al. WO 95/04072.

Compounds which contain so-called "carboxylate equivalents" (as previously defined) can be prepared in a variety of ways. For example, hydroxamic acids can be prepared from the corresponding carboxylic acids by conversion to the N-hydroxysuccinimide ester followed by treatment with hydroxylamine. Amides are accessible by treatment of a methyl ester with ammonia in methanol.

The present compounds are useful as pharmaceuticals for the treatment of various conditions in which the use of a glycine transport inhibitor is indicated. Certain compounds of the invention are useful as pharmaceuticals for the treatment of conditions in which the use of a mixed GlyT-2 glycine transport inhibitor and GAT inhibitor is indicated, and still other compounds of the invention are useful as pharmaceuticals for the treatment of various conditions in which the use of a mixed GlyT-1 and GlyT-2 glycine transport inhibitor is indicated is indicated.

Preferred compounds are those useful as pharmaceuticals for the treatment of medical conditions for which GlyT-2-mediated inhibition of glycine transport is needed, such as the treatment of pain or the treatment of diseases or conditions associated with increased muscle contraction, for example spasticity and myoclonus. Spasticity that can be treated via modulation of glycine transporters is that associated with epilepsy, stroke, head trauma, multiple sclerosis, spinal cord injury, dystonia, and other conditions of illness and injury of the nervous system. By GlyT-2 we mean those glycine transporters found predominantly in the brain stem and spinal cord and the distribution of which corresponds closely to that of strychnine-sensitive glycine receptors (Liu et al. *J. Biological Chemistry*, 268, 1993:22802–22808; Jursky and Nelson, J. Neurochemistry, 64,1995:1026–1033).

For use in medicine, the compounds of the present invention can be administered in a standard pharmaceutical composition. The present invention therefore provides, in a further aspect, pharmaceutical compositions comprising a pharmaceutically acceptable carrier and a Formula VI compound or a pharmaceutically acceptable salt, solvate or hydrate thereof, in an amount effective to treat the target indication.

The compounds of the present invention may be administered by any convenient route, for example by oral, parenteral, buccal, sublingual, nasal, rectal, patch, pump or transdermal administration and the pharmaceutical compositions formulated accordingly.

Compounds of Formula I and VI and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

The physician or other health care professional can select the appropriate dose and treatment regimen based on the subject's weight, age and physical condition. Dosages will generally be selected to maintain a serum level of compounds in the invention between about 0.01 $\mu$g/cc and about 1000 $\mu$g/cc, preferably between about 0.1 $\mu$g/cc and 100 $\mu$g/cc. For parenteral administration, an alternative measure of preferred amount is from about 0.001 mg/kg to about 10 mg/kg (alternatively, from about 0.01 mg/kg to about 10 mg/kg), more preferably from about 0.01 mg/kg to about 1 mg/kg (from about 0.1 mg/kg to about 1 mg/kg), will be administered. For oral administrations, an alternative measure of preferred administration amount is from about 0.001 mg/kg to about 10 mg/kg (from about 0.1 mg/kg to about 10 mg/kg), more preferably from about 0.01 mg/kg to about 1 mg/kg (from about 0.1 mg/kg to about 1 mg/kg). For administrations in suppository form, an alternative measure of preferred administration amount is from about 0.1 mg/kg to about 10 mg/kg, more preferably from about 0.1 mg/kg to about 1 mg/kg.

SPECIFIC EXAMPLES

Starting substituted thiophenes:

Example (a)

2-Bromo-3-phenylthiophene (Tamao, K. et al., Nickel-phosphine complex-catalyzed Grignard coupling-II, Tetrahedron, 1982, 38, 3347–3354 ; Buvat, P. et al., P., Enhanced infrared properties of regioregular poly(3-alkylthiophenes), Macromolecules, 1997, 30, 2685–2692)

To a mixture of 1.0 mL (10.6 mmol) of 3-bromothiophene, 20 mL of anhydrous ether, 60 mg (0.11 mmol) of 1,3-[Bis(diphenylphosphino)-propane] dichloronickel(II)[NiCl$_2$(dppp)] under N$_2$ with stirring at 0° C. was slowly added 7.0 mL (14 mmol) of 2.0 M PhMgCl in THF. The reaction was slowly warmed to room temperature. Note that a vigorous exothermic reaction may occur if the Grignard reagent is added too fast or if the reaction is allowed to warm to room temperature to rapidly. After stirring for 3 h, the mixture was warmed to reflux for 2 h, poured into 20 mL of 5% HCl solution, and extracted with 2×20 mL of ether. The combined organic phases were washed with 15 mL of H$_2$O and 15 mL of brine, dried (MgSO$_4$) and concentrated. Crystallization from hexanes provided 0.58 g (34% yield) of 3-phenylthiophene.

3-Phenylthiophene (0.58 g, 3.62 mmol) was dissolved in 15 mL of a 1:1 solution of CHCl$_3$ and AcOH followed by the portion-wise addition of 0.77 g (4.3 mmol) of NBS. The mixture was stirred at room temperature for 1 h, poured into 25 mL of H$_2$O, and diluted with 30 mL of hexanes. The organic layer was washed successively with 2×10 mL of 10% aqueous KOH solution, 2×10 mL of H$_2$O, and 2×10 mL of brine, and concentrated in vacuo to provide 0.68 g (78% yield) of 2-bromo-3-phenylthiophene as an oil.

In a like manner, the following additional compounds were prepared:
(b) 2-Bromo-3-ethylthiophene;
(c) 2-Bromo-3-cyclopentylthiophene;
(d) 2-Bromo-3-propylthiophene;
(e) 2-Bromo-3-(4-fluorophenyl)thiophene; and
(f) 2-Bromo-3-(4-methoxyphenyl)thiophene Starting Fluorenones:

Method A

Example (a)

1-Methyl-9-fluorenone: In an oven dried flask flushed with N$_2$ was combined 2.7 g (20.0 mmol) of 3-methylbenzeneboronic acid, 3.64 g (15 mmol) of 2-iodobenzoic acid, 150 mL of DME, 26 mL of 10% Na$_2$CO$_3$ and 600 mg (0.5 mmol) of Pd(PPh$_3$)$_4$. The mixture was warmed to reflux for 24 h and partitioned between 100 mL of NaHCO$_3$ and 100 mL of ether. The ether layer was extracted with 2×50 mL of NaHCO$_3$ and the combined NaHCO$_3$ fractions were washed with 2×50 mL of ether, acidified with 10% HCl and extracted with 3×75 mL of ether. The combined ether extracts were washed with 50 mL of H$_2$O, 50 mL of brine, dried (MgSO$_4$) and concentrated in vacuo. The oil was crystallized from ether/hexanes (1/1) at −20° C. as a white precipitate, which after filtration, provided 1.32 g (41% yield) of 3'-methyl-2-biphenylcarboxylic acid as a brown oil.

A mixture of 1.32 g (6.2 mmol) of 3'-methyl-2-biphenylcarboxylic acid, 40 mL of CH$_2$Cl$_2$ and 0.70 mL (9.6 mmol) of SOCl$_2$ was warmed to reflux for 2 h. The solution was cooled to room temperature and 1.10 mL (9.4 mmol) of SnCl$_4$ was added dropwise with stirring. The dark brown homogenous mixture was stirred for 18 h, poured into 50 mL of cold saturated aqueous NaHCO$_3$, and extracted with 2×50 mL of ether. The ether extracts were combined and washed with 30 mL of saturated NaHCO$_3$ solution, 30 mL of H$_2$0 and 30 mL of brine, dried (MgSO$_4$) and concentrated in vacuo. Chromatography over SiO$_2$ (Biotage 40 S) using 1% EtOAc in hexanes provided 168 mg (16% yield) of 1-methyl-9-fluorenone (Ladd, D. L. et al., Synthesis and dopaminergic binding of 2-aryldopamine analogues: Phenethylamines, 3-benzazepines, and 9-(aminomethyl) fluorenes. *J. Med. Chem.* 1986, 29, 1904–1912).

Method B

Example (b)

3-Methyl-9-fluorenone: A suspension of 156 mg (0.77 mmol) of iodobenzene and 50 mg (0.05 mmol) of Pd(PPh$_3$)$_4$ in 4 mL of DME was stirred for 10 minutes at room temperature. The mixture was treated with a solution of 0.96 g (5 mmol) of 5-methyl-2-carbox-N,N-diethylamidophenylboronic acid (Sharp, M. J. et al., Synthetic connections to the aromatic directed metalation reaction. Unsymmetrical biaryls by palladium-catalyzed cross coupling of directed metalation-derived arylboronic acids with aryl halides. *Tetrahedron Lett.,* 1985, 26, 5997–6000) in 1 mL of DME and then with 1.75 mL of 2N Na$_2$CO$_3$. The reaction was warmed to reflux for 18 h, poured into 25 mL of 10% Na$_2$CO$_3$, and extracted with 3×50 mL of ether. The combined ether extracts were washed with 30 mL of H$_2$0 and 30 mL of brine, dried (MgSO$_4$) and concentrated in vacuo. Chromatography over SiO$_2$ (Biotage flash 12) using 15% EtOAc in hexanes as eluent provided 195 mg (95% yield) of 2-carboxy-N,N-diethylamido-5-methyl-1,1'-biphenyl.

A solution of 550 mg (2.1 mmol) of 2-carboxy-N,N-diethylamido-5-methyl-1,1'-biphenyl in 100 mL of anhydrous THF was cooled to 0° C. and 2.8 mL (4.2 mmol) of 1.5M LDA was added dropwise. The reaction was slowly warmed to room temperature, stirred for 18 h, poured into 50 mL of H$_2$O, and extracted with 2×50 mL of ether. The combined ether extracts were washed with 25 mL of 1 N HCl, 25 mL of saturated aqueous NaHCO$_3$, 25 mL of H$_2$O, and 25 mL of brine, dried (MgSO$_4$) and concentrated in vacuo. Purification over SiO$_2$ (Biotage 40 S) using 5% EtOAc in hexanes provided 125 mg (31% yield) of 3-methyl-9-fluorenone.

In a like manner, the following additional compounds were prepared:
(c) 4-Methyl-9-fluorenone: from 2-methylbenzeneboronic acid and 2-iodobenzoic acid following method A;
(d) 2-Methyl-9-fluorenone: from 4-methylbenzeneboronic acid and 2-iodobenzoic acid following method A;
(e) 2-Phenyl-9-fluorenone: from 4-phenylbenzeneboronic acid and 2-iodobenzoic acid following method A;
(f) 2-Methoxy-9-fluorenone: from 4-methoxybenzeneboronic acid and 2-iodobenzoic acid following method A;
(g) 2-tert-Butyl-9-fluorenone: from 4-tert-butylbenzeneboronic acid and 2-iodobenzoic acid following method A;
(h) 2-Ethyl-9-fluorenone: from 4-ethylbenzeneboronic acid and 2-iodobenzoic acid following method A; and
(i) Benzo[b]indeno[1,2-d]thiophen-9-one: from 2-benzo[b]thiopheneboronic acid and 2-iodobenzoic acid following method A.

Example 1(a)

9-(3-Methylphenyl)-9H-fluoren-9-ol

A 1.0 M solution of m-tolylmagnesium chloride in tetrahydrofuran (10 mL, 10 mmol) (Aldrich) was added dropwise to a solution of 9-fluorenone (1.8 g, 10 mmol) (Aldrich) in anhydrous tetrahydrofuran (5 mL) with stirring under argon at 0° C. The mixture was stirred at room temperature for 1 h, anhydrous diethyl ether (20 mL) was added and the formed precipitate was filtered and dissolved in chloroform (50 mL). The chloroform solution was washed with a saturated solution of ammonium chloride (10 mL), brine (10 mL), dried (MgSO$_4$), the solvent evaporated and the residue recrystallized from diethyl ether/hexane to give the title compound as a white solid (2.42 g, 89%).

In a like manner, the following additional compounds were prepared:
(j) 9-Phenyl-9H-fluoren-9-ol (yield 57%): from phenylmagnesium chloride and 9-fluorenone;
(k) 9-(4-Methylphenyl)-9H-fluoren-9-ol (yield 39%): from p-tolylmagnesium bromide and 9-fluorenone;
(l) 9-(2,4,6-Trimethylphenyl)-9H-fluoren-9-ol (yield 82%): from 2-mesitylmagnesium bromide and 9-fluorenone;
(m) 2-Fluoro-9-phenyl-9H-fluoren-9-ol: from phenylmagnesium bromide and 2-fluoro-9-fluorenone;
(n) 9-Phenyl-9H-xanthen-9-ol: from phenylmagnesium chloride and xanthone;
(o) 9-(4-Chlorophenyl)-9H-fluoren-9-ol: from 4-chlorophenylmagnesium bromide and 9-fluorenone;
(p) 9-(3-Methylphenyl)-9H-xanthen-9-ol: from m-tolylmagnesium chloride and xanthone;
(q) 9-Phenyl-9H-thioxanthen-9-ol: from phenylmagnesium chloride and thioxanthen-9-one;
(r) 10,10-Dimethyl-9-phenyl-9,10-dihydroanthracen-9-ol: from phenylmagnesium chloride and 10,10-dimethyl-9,10-dihydroanthracen-9-one;
(s) 9-(3-Methylphenyl)-9H-thioxanthen-9-ol: from m-tolylmagnesium chloride and thioxanthen-9-one;
(t) 2,7-Dichloro-9-phenyl-9H-fluoren-9-ol: from phenylmagnesium chloride and 2,7-dichloro-9-fluorenone;
(u) 9-(4-Fluorophenyl)-9H-xanthen-9-ol: from 4-fluorophenylmagnesium bromide and xanthone;
(v) 10,11-Dihydro-5-phenyl-5H-dibenzo[a,d]cyclohepten-5-ol: from phenylmagnesium chloride and dibenzosuberone;
(w) 5-Phenyl-5H-dibenzo[a,d]cyclohepten-5-ol: from phenylmagnesium chloride and dibenzosuberenone;
(x) 9-(4-Methylphenyl)-9H-thioxanthen-9-ol: from p-tolylmagnesium bromide and thioxanthen-9-one;
(y) 9-(4-Methylphenyl)-9H-xanthen-9-ol: from p-tolylmagnesium bromide and xanthone;
(z) 9-Cyclohexyl-9H-fluoren-9-ol: from cyclohexylmagnesium chloride and 9-fluorenone;
(aa) 5-(3-Methylphenyl)-5H-dibenzo[a,d]cyclohepten-5-ol: m-tolylmagnesium chloride and dibenzosuberenone;
(bb) 5-(4-Methylphenyl)-5H-dibenzo[a,d]cyclohepten-5-ol: from p-tolylmagnesium bromide and dibenzosuberenone;
(cc) 2,7-Dibromo-9-phenyl-9H-fluoren-9-ol: from phenylmagnesium chloride and 2,7-dibromo-9-fluorenone;
(dd) 7-phenyl-7H-benz[d,e]anthracen-7-ol: from phenylmagnesium chloride and benzanthrone;
(ee) 9-Phenylmethyl-9H-fluoren-9-ol: from benzylmagnesium chloride and 9-fluorenone;
(ff) 9-t-Butyl-9H-fluoren-9-ol: from t-butylmagnesium chloride and 9-fluorenone;
(gg) 9-(4-Fluorophenyl)-9H-fluoren-9-ol: from 4-fluoromagnesium bromide and 9-fluorenone;
(hh) 4-methyl-9-phenyl-9H-fluoren-9-ol: from phenylmagnesium chloride and 4-methyl-9-fluorenone;
(ii) 3-methyl-9-phenyl-9H-fluoren-9-ol: from phenylmagnesium chloride and 3-methyl-9-fluorenone;
(jj) 1-methyl-9-phenyl-9H-fluoren-9-ol: from phenylmagnesium chloride and 1-methyl-9-fluorenone;
(kk) 9-(1-naphthyl)-2-phenyl-9H-fluoren-9-ol: from 1-naphthylmagnesium chloride and 2-phenyl-9-fluorenone;
(ll) 2-methoxy-9-phenyl-9H-fluoren-9-ol: from phenylmagnesium chloride and 2-methoxy-9-fluorenone;
(mm) 2-tert-butyl-9-phenyl-9H-fluoren-9-ol: from phenylmagnesium chloride and 2-tert-butyl-9-phenyl-9-fluorenone;
(nn) 2-methyl-9-phenyl-9H-fluoren-9-ol: from phenylmagnesium chloride and 2-methyl-9-fluorenone;
(oo) 2-ethyl-9-phenyl-9H-fluoren-9-ol: from phenylmagnesium chloride and 2-ethyl-9-fluorenone;
(pp) 2-phenyl-9-phenyl-9H-fluoren-9-ol: from phenylmagnesium chloride and 2-phenyl-9-fluorenone;
(qq) 8-Phenyl-8H-indeno[2,1-b]thiophen-8-ol: from phenylmagnesium chloride and indeno[2,1-b]thiophen-8-one (prepared as described in Rawson and Wyberg, *Rec. Trav. Chim.* 90, 1971:46–55)

Example 2(a)

9-(2-Methylthien-5-yl)-9H-fluoren-9-ol

A 2.5M solution of butyllithium in hexanes (9.6 mL, 24 mmol), (Aldrich) was added dropwise to a solution of 2-methylthiophene (1.96 g, 20 mmol) in anhydrous tetrahydrofuran (10 mL) with stirring under argon at 0° C. The mixture was stirred at room temperature for 0.5 h and then cooled to 0° C. A solution of 9-fluorenone (3.6 g, 20 mmol), (Aldrich) in anhydrous tetrahydrofuran (5 mL) was added dropwise to the mixture with stirring and cooling at 0° C. The reaction mixture was stirred at room temperature for 1 h, poured into a saturated solution of ammonium chloride (5 mL) and extracted with dichloromethane (3×20 mL). The combined dichloromethane extracts were washed with brine (10 mL), dried (MgSO$_4$), the solvent evaporated and the residue chromatographed on silica gel column with 10% ethyl acetate in hexanes to give the title compound as an oil.

In a like manner, the following additional compounds were prepared:
(b) 9-(2-Thienyl)-9H-fluoren-9-ol: from thiophene and 9-fluorenone;
(c) 5-(2-Thienyl)-5H-dibenzo[a,d]cyclohepten-5-ol: from thiophene and dibenzosuberenone;
(d) 10,11-Dihydro-5-(2-thienyl)-5H-dibenzo[a,d]cyclohepten-5-ol: from thiophene and dibenzosuberone;
(e) 9-(3-phenylthien-2-yl)-9H-fluoren-9-ol: from 2-bromo-3-phenyl-thiophene and 9-fluorenone;
(f) 9-(3-ethylthien-2-yl)-9H-fluoren-9-ol: from 2-bromo-3-ethylthiophene and 9-fluorenone;
(g) 9-(3-propylthien-2-yl)-9H-fluoren-9-ol: from 2-bromo-3-propylthiophene and 9-fluorenone;
(h) 9-(3-cyclopentylthien-2-yl)-9H-fluoren-9-ol: from 2-bromo-3-cyclopentylthiophene and 9-fluorenone;
(i) 2-methoxy-9-(2-thienyl)-9H-fluoren-9-ol: from 2-thienyllithium and 2-methoxy-9-fluorenone;
(j) 2-phenyl-9-(2-thienyl)-9H-fluoren-9-ol: from 2-thienyllithium and 2-phenyl-9-fluorenone;
(k) 2-tert-butyl-9-(2-thienyl)-9H-fluoren-9-ol: from 2-thienyllithium and 2-tert-butyl-9-fluorenone;
(l) 2-ethyl-9-(2-thienyl)-9H-fluoren-9-ol: from 2-thienyllithium and 2-ethyl-9-fluorenone;
(m) 2-methyl-9-(2-thienyl)-9H-fluoren-9-ol: from 2-thienyllithium and 2-methyl-9-fluorenone; and
(n) 9-(Benzo[b]thien-2-yl)-9H-fluoren-9-ol: from benzo[b]thiophene (thianaphthene) and 9-fluorenone;

Example 3(a)

9-(3-Chlorophenyl)-9H-fluoren-9-ol

A 2.5M solution of butyllithium in hexanes (1.8 eq), (Aldrich) was added dropwise to a solution of 1-bromo-3-chlorobenzene (1.5 eq) in anhydrous diethyl ether with stirring under argon at −40° C. After stirring at room temperature for 0.5 h, a solution of 9-fluorenone (1 eq), (Aldrich) in anhydrous diethyl ether was added dropwise to the mixture with stirring and cooling at 0° C. The reaction mixture was stirred at room temperature for 1 h, poured into a saturated solution of ammonium chloride and extracted with dichloromethane. The combined dichloromethane extracts were washed with brine, dried (MgSO$_4$), the solvent evaporated and the residue chromatographed on silica gel column with 10% ethyl acetate in hexanes to give the title compound as an oil.

In a like manner, the following additional compounds were prepared:
(b) 10,11-Dihydro-5-(2-thienyl)-5H-dibenzo[a,d]cyclohepten-5-ol: from 2-bromothiophene and dibenzosuberone;
(c) 9-(2-Fluorophenyl)-9H-fluoren-9-ol: from 1-bromo-2-fluorobenzene and 9-25 fluorenone;
(d) 9-(3,4-Methylenedioxyphenyl)-9H-fluoren-9-ol: from 4-bromo-1,2-(methylenedioxy)benzene and 9-fluorenone;
(e) 9-(3-Chlorophenyl)-9H-fluoren-9-ol: from 1-bromo-3-chlorobenzene and 9-fluorenone;
(f) 9-(3-Methoxyphenyl)-9H-fluoren-9-ol. from 3-bromoanisole and 9-fluorenone;
(g) 9-(2-Methylphenyl)-9H-fluoren-9-ol: from 2-bromotoluene and 9-fluorenone;
(h) 9-Butyl-9H-fluoren-9-ol: from butyllithium and 9-fluorenone;
(i) 9-(3,4-Dimethoxyphenyl)-9H-fluoren-9-ol: from 4-bromoveratrole and 9-fluorenone;
(j) 9-(3-Methylthien-2-yl)-9H-fluoren-9-ol: from 2-bromo-3-methyl-thiophene and 9-fluorenone;
(k) 9-(2-Methoxyphenyl)-9H-fluoren-9-ol: from 2-bromoanisole and 9-fluorenone;
(l) 9-(5-Chlorothien-2-yl)-9H-fluoren-9-ol: from 2-bromo-5-chlorothiophene and 9-fluorenone;
(m) 9-(3-Trifluoromethylphenyl)-9H-fluoren-9-ol: from 3-bromobenzotrifluoride and 9-fluorenone;
(n) 9-(4-Methoxyphenyl)-9H-fluoren-9-ol: from 4-bromoanisole and 9-fluorenone;
(o) 9-(4-Ethylphenyl)-9H-fluoren-9-ol: from 1-bromo-4-ethylbenzene and 9-fluorenone;
(p) 9-(2-Naphthyl)-9H-fluoren-9-ol: from 2-bromonaphthalene and 9-fluorenone;
(q) -(3-Biphenyl)-9H-fluoren-9-ol: from 3-bromobiphenyl and 9-fluorenone;
(r) 9-(3-Ethylphenyl)-9H-fluoren-9-ol: from 1-bromo-3-ethylbenzene and 9-fluorenone;
(s) 9-(3,4-dimethylphenyl)-9H-fluoren-9-ol: from 1-bromo-3,4-dimethylbenzene and 9-fluorenone;
(t) 9-(2-ethylphenyl)-9H-fluoren-9-ol: from 1-bromo-2-ethylbenzene and 9-fluorenone; and
(u) 9-(2-Biphenyl)-9H-fluoren-9-ol: from 2-bromobiphenyl and 9-fluorenone;
(v) 9-[3-(4-Fluorophenyl)thien-2-yl]-9H-fluoren-9-ol: from 2-bromo-3-(4-fluorophenyl)thiophene and 9-fluorenone;
(w) 9-[3-(4-Methoxyphenyl)thien-2-yl]-9H-fluoren-9-ol: from 2-bromo-3-(4-methoxyphenyl)thiophene and 9-fluorenone;
(x) 9-(2-Biphenyl)-9H-fluoren-9-ol: from 2-bromobiphenyl and 9-fluorenone; and
(y) 9-[(1-Phenylsulfonyl)indol-5-yl]-9H-fluoren-9-ol: from 5-bromo-1-(phenylsulfonyl)indole and 9-fluorenone;

Example 4(a)

O-(9-Phenyl-9H-fluoren-9-yl)-L-serine

Step 1: N$^\alpha$-(9-Fluorenylmethoxycarbonyl)—O—(9-phenyl-9H-fluoren-9-yl)-L-serine methyl ester Method A:

A solution of 6.2 g (24 mmol) of 9-phenyl-9H-fluoren-9-ol (Example 1b) and 6.8 g (20 mmol) of N$^\alpha$-(9-fluorenylmethoxycarbonyl)-L-serine methyl ester in benzene (150 mL) was placed in a round bottomed flask fitted with a Dean-Stark trap. Two drops of concentrated sulfuric acid were added and the mixture heated under reflux with stirring for 1 h. Removal of the solvent under vacuo gave the crude N$^\alpha$-(9-fluorenylmethoxycarbonyl)—O—(9-phenyl-9H-fluoren-9-yl)-L-serine methyl ester which was subjected to the Fmoc deprotection in Step 2 without further purification.

Method B:

To a mixture of 0.17 g (0.5 mmol) N$^\alpha$-(9-fluorenylmethoxycarbonyl)-L-serine methyl ester, 0.043 g (0.6 mmol) potassium carbonate and 0.083 g (0.5 mmol) potassium iodide in acetonitrile (2 mL) was added 0.16 g (0.5 mmol) of 9-bromo-9-phenyl-9H-fluorene (Aldrich), and the mixture stirred at 40° C. for 2 h. Filtration and removal of the solvent under vacuo gave the crude N$^\alpha$-(9-fluorenylmethoxycarbonyl)-O-(9-phenyl-9H-fluoren-9-yl)-L-serine methyl ester which was subjected to the Fmoc deprotection in Step 2 without further purification.

Step 2: O-(9-Phenyl-9H-fluoren-9-yl)-L-serine methyl ester

The crude $N^\alpha$-(9-fluorenylmethoxycarbonyl)-O-(9-phenyl-9H-fluoren-9-yl)-L-serine methyl ester from Step 1 (Method A) was dissolved in piperidine (5 mL) and the mixture stirred at 60 (C for 0.5 h. After evaporation of the solvent the residue was chromatographed on silica gel with ethyl acetate to give 6.96 g (yield 97%) O-(9-phenyl-9H-fluoren-9-yl)-L-serine methyl ester as a viscous oil. $^1$H NMR (CDCl$_3$, 300 MHz) δ: 7.65 (d, 2H), 7.40–7.05 (m, 11H), 3.65 (s, 3H), 3.46 (t, 1H), 3.30–3.10 (m, 2H), 1.80 (br s, 2H); $^{13}$C NMR (CDCl$_3$, 75 MHz) δ: 174.1, 146.4, 146.2, 142.7, 140.4, 129.0, 128.9, 128.1, 127.9, 126.9, 125.2, 125.1, 124.9, 119.8, 119.7, 88.1, 65.1, 54.6, 51.8, 51.7, 13.9.

Analogous Fmoc deprotection of the crude $N^\alpha$-(9-fluorenylmethoxycarbonyl)-O-(9-phenyl-9H-fluoren-9-yl)-L-serine methyl ester from Step 1 (Method B) gave product identical with the O-(9-phenyl-9H-fluoren-9-yl)-L-serine methyl ester prepared in Step 2, after comparison of the NMR spectra and TLC (60% ethyl acetate in hexanes, Rf=0.3)

Step 3: O-(9-Phenyl-9H-fluoren-9-yl)-L-serine

To a solution of 6.4 g (17.8 mmol) of O-(9-phenyl-9H-fluoren-9-yl)-L-serine methyl ester from step 2 in methanol (20 mL) was added 20% sodium hydroxide (10 mL) and the mixture stirred at room temperature for 1 h. Most of the methanol was evaporated under vacuo, the residue suspended in water (200 mL) and extracted with diethyl ether (2×50 mL). The alkaline aqueous phase was added dropwise into 20% acetic acid (30 mL) with stirring and cooling with an ice bath, the white precipitate was filtered, washed with water and dried in vacuo over P$_2$O$_5$ to give 5.3 g (yield 90%) of O-(9-phenyl-9H-fluoren-9-yl)-L-serine as a white powder. $^{13}$C NMR (DMSO-d$_6$, 75 MHz) δ: 167.0, 146.4, 146.1, 143.3, 140.3, 140.0, 129.4, 129.2, 128.4, 128.2, 128.0, 127.2, 125.6, 125.5, 125.1, 120.5, 120.4, 88.4, 63.2, 54.8.

In a like manner, the following additional compounds were prepared:

(b) O-(9-Phenyl-9H-fluoren-9-yl)-L-threonine: from 9-phenyl-9H-fluoren-9-ol (Example 1b) and $N^\alpha$-(9-fluorenylmethoxycarbonyl)-L-threonine methyl ester;

(c) O-[9-(2-Thienyl)-9H-fluoren-9-yl]-L-serine: from 9-(2-thienyl )-9H-fluoren-9-ol (Example 2b) and $N^\alpha$-(9-fluorenylmethoxycarbonyl)-L-serine methyl ester;

(d) O-(2-Fluoro-9-phenyl-9H-fluoren-9-yl)-L-serine: from 2-fluoro-9-phenyl-9H- fluoren-9-ol (Example 1 e) and $N^\alpha$-(9-fluorenylmethoxycarbonyl)-L-serine methyl ester;

(e) O-[9-(2-Thienyl)-9H-fluoren-9-yl]-L-threonine: from 9-(2-thienyl)-9H-fluoren-9-ol (Example 2b) and $N^\alpha$-(9-fluorenylmethoxycarbonyl)-L-threonine methyl ester;

(f) O-(9-Phenyl-9H-xanthen-9-yl)-L-serine: from 9-phenyl-9H-xanthen-9-ol (Example 1f) and $N^\alpha$-(9-fluorenylmethoxycarbonyl)-L-serine methyl ester;

(g) O-[9-(3-Methylphenyl)-9H-fluoren-9-yl]-L-serine: from 9-(3-methylphenyl)-9H-fluoren-9-ol (Example 1a) and $N^\alpha$-(9-fluorenylmethoxycarbonyl)-L-serine methyl ester.

(h) O-[9-(4-Fluorophenyl)-9H-fluoren-9-yl]-L-serine: from 9-(4-fluorophenyl)-9H-fluoren-9-ol (Example 1y) and $N^\alpha$-(9-fluorenyl-methoxycarbonyl)-L-serine methyl ester;

(i) O-[9-(4-Fluorophenyl)-9H-fluoren-9-yl]-L-threonine: from 9-(4-fluorophenyl)-9H-fluoren-9-ol (Example 1 y) and $N^\alpha$-(9-fluorenylmethoxycarbonyl)-L-threonine methyl ester;

(j) O-(9-Phenyl-9H-xanthen-9-yl)-L-threonine: from 9-phenyl-9H-xanthen-9-ol (Example 2f) and $N^\alpha$-(9-fluorenylmethoxycarbonyl)-L-threonine methyl ester;

(k) O-[9-(4-Chlorophenyl)-9H-fluoren-9-yl]-L-serine: from 9-(4-chlorophenyl)-9H-fluoren-9-ol (Example 2g) and $N^\alpha$-(9-fluorenyl-methoxycarbonyl)-L-serine methyl ester;

(l) O-[5-(2-Thienyl)-5H-dibenzo[a,d]cyclohepten-5-yl]-L-serine: from 5-(2-thienyl)-5H-dibenzo[a,d]cyclohepten-5-ol (Example 2c) and $N^\alpha$-(9-fluorenylmethoxycarbonyl)-L-serine methyl ester;

(m) O-[9-(3-Methylphenyl)-9H-xanthen-9-yl]-L-serine: from 9-(3-methylphenyl)-9H-xanthen-9-ol (Example lh) and $N^\alpha$-(9-fluorenylmethoxycarbonyl)-L-serine methyl ester;

(n) O-[9-(4-Methylphenyl)-9H-fluoren-9-yl]-L-serine: from 9-(4-methylphenyl)-9H-fluoren-9-ol (Example 1 c) and $N^\alpha$-(9-fluorenylmethoxycarbonyl)-L-serine methyl ester;

(o) O-[9-(2-Methylthien-5-yl)-9H-fluoren-9-yl]-L-serine: from 9-(2-methylthien-5-yl)-9H-fluoren-9-ol (Example 2a) and $N^\alpha$-(9-fluorenylmethoxycarbonyl)-L-serine methyl ester;

(p) O-(9-Phenyl-9H-thioxanthen-9-yl)-L-serine: from 9-phenyl-9H-thioxanthen-9-ol (Example 1i) and $N^\alpha$-(9-fluorenylmethoxycarbonyl)-L-serine methyl ester;

(q) O-[9-(3-Methylphenyl)-9H-xanthen-9-yl]-L-threonine: from 9-(3-methylphenyl)-9H-xanthen-9-ol (Example 1 h) and $N^\alpha$-(9-fluorenylmethoxycarbonyl)-L-threonine methyl ester;

(r) O-(10,10-Dimethyl-9-phenyl-9,10-dihydroanthracen-9-yl)-L-serine: from 10,10-dimethyl-9-phenyl-9,10-dihydroanthracen-9-ol (Example 1j) $N^\alpha$-(9-fluorenylmethoxycarbonyl)-L-serine methyl ester;

(s) O-[9-(3-Methylphenyl)-9H-thioxanthen-9-yl]-L-serine: from 9-(3-methylphenyl)-9H-thioxanthen-9-ol (Example 1k) and $N^\alpha$-(9-fluorenylmethoxycarbonyl)-L-serine methyl ester;

(t) O-[9-(4-Chlorophenyl)-9H-fluoren-9-yl]-L-threonine: from 9-(4-chlorophenyl)-9H-fluoren-9-ol (Example 1 g) and $N^\alpha$-(g- fluorenylmethoxycarbonyl)-L-threonine methyl ester;

(u) O-(2,7-Dichloro-9-phenyl-9H-fluoren-9-yl)-L-serine: from 2,7-dichloro-9-phenyl-9H-fluoren-9-ol (Example 1l) and $N^\alpha$-(9-fluorenylmethoxycarbonyl) L-serine methyl ester;

(v) β-(9-Phenyl-9H-fluoren-9-yl)oxy-DL-β-hydroxynorvaline; from 9-phenyl-9H-fluoren-9-ol (Example 1 b) and $N^\alpha$-(9-fluorenylmethoxycarbonyl)-DL-β-hydroxynorvaline methyl ester;

(w) O-(9-Phenyl-9H-fluoren-9-yl)-L-allothreonine: from 9-phenyl-9H-fluoren-9-ol (Example 1b) and $N^\alpha$-(9-fluorenylmethoxycarbonyl)-L-allothreonine methyl ester;

(x) O-[9-(4-Fluorophenyl)-9H-xanthen-9-yl]-L-threonine: from 9-(4-fluorophenyl)-9H-xanthen-9-ol (Example 1 m) and N—(9-fluorenylmethoxycarbonyl)-L-threonine methyl ester;

(y) O-(10,11-Dihydro-5-phenyl-5H-dibenzo[a,d]cyclohepten-5-yl)-L-serine: from 10,11-dihydro-5-phenyl-5H-dibenzo[a,d]cyclohepten-5-ol (Example 1n) and $N^\alpha$-(9-fluorenylmethoxycarbonyl)-L-serine methyl ester;

(z) O-(5-Phenyl-5H-dibenzo[a,d]cyclohepten-5-yl)-L-serine: from 5-phenyl-5H-dibenzo[a,d]cyclohepten-5-ol (Example 1o) and $N^\alpha$-(9-fluorenylmethoxycarbonyl)-L-serine methyl ester;

(aa) O-[9-(4-Methylphenyl)-9H-thioxanthen-9-yl]-L-serine: from 9-(4-methylphenyl)-9H-thioxanthen-9-ol (Example 1p) and $N^\alpha$-(9-fluorenylmethoxycarbonyl)-L-serine methyl ester;

(bb) O-[9-(4-Methylphenyl)-9H-xanthen-9-yl]-L-serine: from 9-(4-methylphenyl)-9H-xanthen-9-ol (Example 1q) and $N^\alpha$-(9-fluorenylmethoxycarbonyl)-L-serine methyl ester;

(cc) O-(9-Phenyl-9H-fluoren-9-yl)-DL-threo-3-phenylserine: from 9-phenyl-9H-fluoren-9-ol (Example 1 b) and $N^\alpha$-(9-fluorenylmethoxycarbonyl)-DL-threo-3-phenylserine methyl ester;

(dd) O-[9-(4-Fluorophenyl)-9H-xanthen-9-yl]-L-serine: from 9-(4-fluorophenyl)-9H-xanthen-9-ol (Example 1 m) and $N^\alpha$-(9-fluorenylmethoxycarbonyl)-L-serine methyl ester;

(ee) O-[10,11-Dihydro-5-(2-thienyl)-5H-dibenzo[a,d] cyclohepten-5-yl]-L-serine: from 10,11-dihydro-5-(2-thienyl)-5H-dibenzo[a,d]cyclohepten-5-ol (Example 2d) and $N^\alpha$-(9-fluorenylmethoxycarbonyl)-L-serine methyl ester;

(ff) O-(9-Cyclohexyl-9H-fluoren-9-yl)-L-serine: from 9-cyclohexyl-9H-fluoren-9-ol (Example 1r) and $N^\alpha$-(9-fluorenylmethoxycarbonyl)-L-serine methyl ester;

(gg) O-(9-Phenyl-9H-xanthen-9-yl)-D-threonine: from 9-phenyl-9H-xanthen-9-ol (Example 1f) and $N^\alpha$-(9-fluorenylmethoxycarbonyl)-D-threonine methyl ester;

(hh) O-[5-(3-Methylphenyl)-5H-dibenzo[a,d]cyclohepten-5-yl]-L-serine: from 5-(3-methylphenyl)-5H-dibenzo[a,d]cyclohepten-5-ol (Example 1s) and $N^\alpha$-(9-fluorenylmethoxycarbonyl)-L-serine methyl ester;

(ii) O-[5-(4-Methylphenyl)-5H-dibenzo[a,d]cyclohepten-5-yl]-L-serine: from 5-(4-methylphenyl)-5H-dibenzo[a,d]cyclohepten-5-ol (Example 1t) and $N^\alpha$-(9-fluorenylmethoxycarbonyl)-L-serine methyl ester;

(jj) O-(9-Phenyl-9H-xanthen-9-yl)-D-serine: from 9-phenyl-9H-xanthen-9-ol (Example 1f) and $N^\alpha$-(9-fluorenylmethoxycarbonyl)-D-serine methyl ester;

(kk) O-[9-(4-Methylphenyl)-9H-xanthen-9-yl]-D-serine: from 9-(4-methylphenyl)-9H-xanthen-9-ol (Example 1q) and $N^\alpha$-(9-fluorenylmethoxycarbonyl)-D-serine methyl ester;

(ll) O-[9-(3-Methylphenyl)-9H-xanthen-9-yl]-D-serine: from 9-(3-methylphenyl)-9H-xanthen-9-ol (Example 1h) and $N^\alpha$-(9-fluorenylmethoxycarbonyl)-D-serine methyl ester;

(mm) O-(9-Phenyl-9H-fluoren-9-yl)-D-serine: from 9-phenyl-9H-fluoren-9-ol (Example 1b) and $N^\alpha$-(9-fluorenylmethoxycarbonyl)-D-serine methyl ester;

(nn) O-(2,7-Dibromo-9-phenyl-9H-fluoren-9-yl)-L-serine: from 2,7-dibromo-9-phenyl-9H-fluoren-9-ol (Example 1u) and $N^\alpha$-(9-fluorenylmethoxycarbonyl)-L-serine methyl ester;

(oo) O-[9-(2,4,6-Trimethyl phenyl )-9H-fluoren-9-yl]-L-serine: from 9-(2,4,6-trimethylphenyl)-9H-fluoren-9-ol (Example 1d) and $N^\alpha$-(9-fluorenylmethoxycarbonyl )-L-serine methyl ester;

(pp) O-[9-Phenylmethyl-9H-fluoren-9-yl]-L-serine: from 9-phenylmethyl-9H-fluoren-9-ol (Example 1w) and $N^\alpha$-(9-fluorenylmethoxycarbonyl)-L-serine methyl ester;

(qq) O-[9-(2-Fluorophenyl)-9H-fluoren-9-yl]-L-threonine: from 9-(2-fluorophenyl)-9H-fluoren-9-ol (Example 3c) and $N^\alpha$-(9-fluorenylmethoxycarbonyl)-L-threonine methyl ester;

(rr) O-[9-(3,4-Methylenedioxyphenyl)-9H-fluoren-9-yl]-L-threonine: from 9-3,4-methylenedioxyphenyl-9H-fluoren-9-ol (Example 3d) and $N^\alpha$-(9-fluorenylmethoxycarbonyl)-L-threonine methyl ester;

(ss) O-[9-(3-Chlorophenyl)-9H-fluoren-9-yl]-L-threonine: from 9-(3-chlorophenyl)-9H-fluoren-9-ol (Example 3e) and $N^\alpha$-(9-fluorenylmethoxycarbonyl)-L-threonine methyl ester;

(tt) O-[9-(3-Methoxyphenyl)-9H-fluoren-9-yl]-L-threonine: from 9-(3-methoxyphenyl)-9H-fluoren-9-ol (Example 3f) and $N^\alpha$-(9-fluorenylmethoxycarbonyl)-L-threonine methyl ester;

(uu) O-[9-(2-Methylphenyl)-9H-fluoren-9-yl]-L-threonine: from 9-(2-methylphenyl)-9H-fluoren-9-ol (Example 3g) and $N^\alpha$-(9-fluorenyl methoxycarbonyl )-L-threonine methyl ester;

(vv) O-(9-Butyl-9H-fluoren-9-yl)-L-threonine: from 9-butyl-9H-fluoren-9-ol (Example 3h) and $N^\alpha$-(9-fluorenylmethoxycarbonyl)-L-threonine methyl ester;

(ww) O-[9-(3,4-Dimethoxyphenyl)-9H-fluoren-9-yl]-L-threonine: from 9-(3,4-dimethoxyphenyl)-9H-fluoren-9-ol (Example 3i) and $N^\alpha$-(9-fluorenylmethoxycarbonyl)-L-threonine methyl ester;

(xx) O-[9-(3-Methylthien-2-yl)-9H-fluoren-9-yl]-L-threonine: from 9-(3-methylthien-2-yl)-9H-fluoren-9-ol (Example 3j) and $N^\alpha$-(9-fluorenylmethoxycarbonyl)-L-threonine methyl ester;

(yy) O-[9-(2-Methoxyphenyl)-9H-fluoren-9-yl]-L-threonine: from 9-(2-methoxyphenyl)-9H-fluoren-9-ol (Example 3k) and $N^\alpha$-(9-fluorenylmethoxycarbonyl)-L-threonine methyl ester;

(zz) O-[9-(5-Chlorothien-2-yl)-9H-fluoren-9-yl]-L-threonine: from 9-(5-chlorothien-2-yl)-9H-fluoren-9-ol (Example 3l) and $N^\alpha$-(9-fluorenylmethoxycarbonyl)-L-threonine methyl ester;

(aaa) O-[9-(3-Trifluoromethylphenyl)-9H-fluoren-9-yl]-L-threonine: from 9-(3-trifluoromethylphenyl)-9H-fluoren-9-ol (Example 3m) and $N^\alpha$-(9-fluorenylmethoxycarbonyl)-L-threonine methyl ester;

(bbb) O-[9-(4-Methoxyphenyl)-9H-fluoren-9-yl]-L-threonine: from 9-(4-methoxyphenyl)-9H-fluoren-9-ol (Example 3n) and $N^\alpha$-(9-fluorenylmethoxycarbonyl)-L-threonine methyl ester;

(ccc) O-[9-(4-Ethylphenyl)-9H-fluoren-9-yl]-L-threonine: from 9-(4-ethylphenyl)-9H-fluoren-9-ol (Example 3o) and $N^\alpha$-(9-fluorenylmethoxycarbonyl)-L-threonine methyl ester;

(ddd) O-[9-(3-Ethylphenyl)-9H-fluoren-9-yl]-L-threonine: from 9-(3-ethylphenyl)-9H-fluoren-9-ol (Example 3r) and $N^\alpha$-(9-fluorenylmethoxycarbonyl)-L-threonine methyl ester;

(eee) O-[9-(2-Naphthyl)-9H-fluoren-9-yl]-L-threonine: from 9-(2-naphthyl)-9H-fluoren-9-ol (Example 3p) and $N^\alpha$-(9-fluorenylmethoxycarbonyl)-L-threonine methyl ester;

(fff) O-[9-(3-biphenyl)-9H-fluoren-9-yl]-L-threonine: from 9-(3-biphenyl)-9H-fluoren-9-ol (Example 3q) and $N^\alpha$-(9-fluorenylmethoxycarbonyl)-L-threonine methyl ester;

(ggg) O-(10,11-Dihydro-5H-dibenzo[a,d]cyclohepten-5-yl)-L-serine: from dibenzosuberol (Aldrich) and $N^\alpha$-(9-fluorenylmethoxycarbonyl)-L-serine methyl ester;

(hhh) O-(9H-fluoren-9-yl)-L-serine: from 9-hydroxyfluorene (Aldrich) and $N^\alpha$-(9-fluorenylmethoxycarbonyl)-L-serine methyl ester;

(iii) O-(9-t-butyl-9H-fluoren-9-yl)-L-serine: from 9-t-butyl-9H-fluoren-9-ol (Example 1x) and $N^\alpha$-(9-fluorenylmethoxycarbonyl)-L-serine methyl ester;

(jjj) O-[9-(3-Phenylthien-2-yl)-9H-fluoren-9-yl]-L-threonine: from 9-(3-phenylthien-2-yl)-9H-fluoren-9-ol and $N^\alpha$-(9-fluorenylmethoxycarbonyl)-L-threonine methyl ester following method A, using trifluoroacetic acid as catalyst in place of $H_2SO_4$;

(kkk) O-[9-(3-Ethylthien-2-yl )-9H-fluoren-9-yl]-L-threonine: from 9-(3-ethylthien-2-yl)-9H-fluoren-9-ol and $N^\alpha$-(9-fluorenylmethoxycarbonyl)-L-threonine methyl ester following method A, using trifluoroacetic acid as catalyst in place of $H_2SO_4$;

(lll) O-[9-(3-Propylthien-2-yl)-9H-fluoren-9-yl]-L-threonine: from 9-(3-propylthien-2-yl)-9H-fluoren-9-ol and $N^\alpha$-(9-fluorenylmethoxycarbonyl)-L-threonine methyl ester following method A, using trifluoroacetic acid as catalyst in place of $H_2SO_4$;

(mmm) O-[9-(3-cyclopentylthien-2-yl)-9H-fluoren-9-yl]-L-threonine: from 9-(3-cyclopentylthien-2-yl)-9H-fluoren- 9-ol and N^α-(9 fluorenylmethoxycarbonyl)-L-threonine methyl ester following method A, using trifluoroacetic acid as catalyst in place of H₂SO₄;

(nnn) O-(4-Methyl-9-phenyl-9H-fluoren-9-yl)-L-threonine: from 4-methyl-9-phenyl-9H-fluoren-9-ol and N^α-(9-fluorenylmethoxycarbonyl)-L-threonine methyl ester following method A using p-toluenesulfonic acid as catalyst in place of H₂SO₄;

(ooo) O-(3-Methyl-9-phenyl-9H-fluoren-9-yl)-L-threonine: from 3-methyl-9-phenyl-9H-fluoren-9-ol and N^α-(9-fluorenylmethoxycarbonyl)-L-threonine methyl ester following method A using p-toluenesulfonic acid as catalyst in place of H₂SO₄;

(ppp) O-(1-Methyl-9-phenyl-9H-fluoren-9-yl)-L-threonine: from 1-methyl-9-phenyl-9H-fluoren-9-ol and N^α-(9-fluorenylmethoxycarbonyl)-L-threonine methyl ester following method A using p-toluenesulfonic acid as catalyst in place of H₂SO₄;

(qqq) O-[9-(1-Naphthyl)-2-phenyl-9H-fluoren-9-yl]-L-threonine: from 9-(1-naphthyl)-2-phenyl-9H-fluoren-9-ol and N^α-(9-fluorenylmethoxycarbonyl)-L-threonine methyl ester following method A using p-toluenesulfonic acid as catalyst in place of H₂SO₄;

(rrr) O-(2-Methoxy-9-phenyl-9H-fluoren-9-yl)-L-threonine: from 2-methoxy-9-phenyl-9H-fluoren-9-ol and N^α-(9-fluorenylmethoxycarbonyl)-L-threonine methyl ester following method A using p-toluenesulfonic acid as catalyst in place of H₂SO₄;

(sss) O-(2-tert-Butyl-9-phenyl-9H-fluoren-9-yl)-L-threonine: from 2-tert-butyl-9-phenyl-9H-fluoren-9-ol and N^α-(9-fluorenylmethoxycarbonyl)-L-threonine methyl ester following method A using p-toluenesulfonic acid as catalyst in place of H₂SO₄;

(ttt) O-[2-Methoxy-9-(2-thienyl)-9H-fluoren-9-yl]-L-threonine: from 2-methoxy-9-(2-thienyl)-9H-fluoren-9-ol and N^α-(9-fluorenylmethoxycarbonyl)-L-threonine methyl ester following method A using p-toluenesulfonic acid as catalyst in place of H₂SO₄;

(uuu) O-[2-Phenyl-9-(2-thienyl )-9H-fluoren-9-yl]-L-threonine: from 2-phenyl-9-(2-thienyl)-9H-fluoren-9-ol and N^α-(9-fluorenylmethoxycarbonyl)-L-threonine methyl ester following method A using p-toluenesulfonic acid as catalyst in place of H₂SO₄;

(vvv) O-[2-tert-Butyl-9-(2-thienyl )-9H-fluoren-9-yl]-L-threonine: from 2-tert-butyl-9-(2-thienyl)-9H-fluoren-9-ol and N^α-(9-fluorenylmethoxycarbonyl)-L-threonine methyl ester following method A using p-toluenesulfonic acid as catalyst in place of H₂SO₄;

(www) O-[2-Ethyl-9-(2-thienyl)-9H-fluoren-9-yl]-L-threonine: from 2-ethyl-9-(2-thienyl)-9H-fluoren-9-ol and N^α-(9-fluorenylmethoxycarbonyl)-L-threonine methyl ester following method A using p-toluenesulfonic acid as catalyst in place of H₂SO₄;

(xxx) O-[2-Methyl-9-(2-thienyl)-9H-fluoren-9-yl]-L-threonine: from 2-methyl-9-(2-thienyl)-9H-fluoren-9-ol and N^α-(9-fluorenylmethoxycarbonyl)-L-threonine methyl ester following method A using p-toluenesulfonic acid as catalyst in place of H₂SO₄;

(yyy) O-(2-Methyl-9-phenyl-9H-fluoren-9-yl)-L-threonine: from 2-methyl-9-phenyl-9H-fluoren-9-ol and N^α-(9-fluorenylmethoxycarbonyl)-L-threonine methyl ester following method A using p-toluenesulfonic acid as catalyst in place of H₂SO₄;

(zzz) O-(2-Ethyl-9-phenyl-9H-fluoren-9-yl)-L-threonine: from 2-ethyl-9-phenyl-9H-fluoren-9-ol and N^α-(9-fluorenylmethoxycarbonyl)-L-threonine methyl ester following method A using p-toluenesulfonic acid as catalyst in place of H₂SO₄;

(aaaa) O-(2-Phenyl-9-phenyl-9H-fluoren-9-yl)-L-threonine: from 2-phenyl-9-phenyl-9H-fluoren-9-ol and N^α-(9-fluorenylmethoxycarbonyl)-L-threonine methyl ester following method A using p-toluenesulfonic acid as catalyst in place of H₂SO₄;

(bbbb) O-[9-(3,4-Dimethylphenyl)-9H-fluoren-9-yl]-L-threonine: from 9-(3,4-dimethylphenyl)-9H-fluoren-9-ol and N^α-(9-fluorenylmethoxycarbonyl)-L-threonine methyl ester following method A using p-toluenesulfonic acid as catalyst in place of H₂SO₄;

(cccc) O-[9-(2-Ethylphenyl)-9H-fluoren-9-yl]-L-threonine: from 9-(2-ethylphenyl)-9H-fluoren-9-ol and N^α-(9-fluorenylmethoxycarbonyl)-L-threonine methyl ester following method A using p-toluenesulfonic acid as catalyst in place of H₂SO₄; and (dddd) O-[9-(2-Biphenyl)-9H-fluoren-9-yl]-L-serine: from 9-(2-biphenyl)-9H-fluoren-9-ol (Example 3u) and N^α-(9-fluorenylmethoxycarbonyl)-L-serine methyl ester following method A, using camphorsulfonic acid as catalyst in place of H₂SO₄;

(eeee) O-[9-(2-Biphenyl)-9H-fluoren-9-yl]-L-threonine: from 9-(2-biphenyl)-9H-fluoren-9-ol (Example 3u) and N^α-(9-fluorenylmethoxycarbonyl)-L-threonine methyl ester following method A, using camphorsulfonic acid as catalyst in place of H₂SO₄;

(ffff) O-[9-Phenyl-9H-fluoren-9-yl]-D,L-α-methylserine: from 9-phenyl-9H-fluoren-9-ol (Example 1b) and N^α-(9-fluorenylmethoxycarbonyl)-D,L-α-methylserine methyl ester following method A, using p-toluenesulfonic acid as catalyst in place of H₂SO₄;

(gggg) O-{9-[3-(4-Fluorophenyl)thien-2-yl]-9H-fluoren-9-yl}-L-threonine: from 9-[3-(4-fluorophenyl)thien-2-yl]-9H-fluoren-9-ol (Example 3v) and N^α-(9-fluorenylmethoxycarbonyl)-L-threonine methyl ester following method A, using trifluoroacetic acid as catalyst in place of H₂SO₄;

(hhhh) O-{9-[3-(4-Methoxyphenyl)thien-2-yl]-9H-fluoren-9-yl}-L-threonine: from 9-[3-(4-methoxyphenyl)thien-2-yl]-9H-fluoren-9-ol (Example 3w) and N^α-(9-fluorenylmethoxycarbonyl)-L-threonine methyl ester following method A, using trifluoroacetic acid as catalyst in place of H₂SO₄;

(iiii) O-[9-(Benzo[b]thien-2-yl)-9H-fluoren-9-yl]-L-threonine: from 9-(benzo[b]thien-2-yl)-9H-fluoren-9-ol (Example 2n) and UW-(9-fluorenylmethoxycarbonyl)-L-threonine methyl ester following method A, using trifluoroacetic acid as catalyst in place of H₂SO₄;

(jjjj) O-[(5-Indolyl)-9H-fluoren-9-yl]-L-threonine: from 9-[(1-phenylsulfonyl)indol-5-yl]-9H-fluoren-9-ol (Example 3aa) and NI-(9-fluorenylmethoxycarbonyl)-L-threonine methyl ester following method A, using trifluoroacetic acid as catalyst in place of H₂SO₄;

(kkkk) O-(8-Phenyl-8H-indeno[2,1-b]thiophen-8-yl)-L-threonine: from 8-phenyl-8H-indeno[2,1-b]thiophen-8-ol (Example 1pp) and N^α-(9-fluorenylmethoxycarbonyl)-L-threonine methyl ester following method A, using trifluoroacetic acid as catalyst in place of H₂SO₄;

(llll) O-(8-Phenyl-8H-indeno[2,1-b]thiophen-8-yl)-L-serine: from 8-phenyl-8H-indeno[2,1-b]thiophen-8-ol (Example 1pp) and 1-(9-fluorenylmethoxycarbonyl)-L-serine methyl ester following method A, using trifluoroacetic acid as catalyst in place of H₂SO₄;

(mmmm) O-(1-Phenyl-9H-fluoren-9-yl)-L-serine: from 1-phenyl-9H-fluoren-9-ol (prepared by NaBH₄ reduction of 1-phenyl-9H-fluoren-9-one) and N^α-(9-fluorenylmethoxycarbonyl)-L-serine methyl ester following method A, using trifluoroacetic acid as catalyst in place of H₂SO₄; and (nnnn) O-(Benzo[b]indeno[1,2-d]thiophen-6-yl)-L-serine: from benzo[b]indeno[1,2-d]thiophen-6-ol (prepared by NaBH$_4$ reduction of benzo[b]indeno[1,2-d]thiophen-9-one (Example i, Starting Fluorenones)) and N$^\alpha$-(9-fluorenylmethoxycarbonyl)-L-serine methyl ester following method A, using trifluoroacetic acid as catalyst in place of H$_2$SO$_4$.

Example 5(a)

N-Methyl—O—(9-phenyl-9H-fluoren-9-yl)-L-serine
Step 1:

To a mixture of 0.8 g (2.2 mmol) of O-(9-phenyl-9H-fluoren-9-yl)-L-serine methyl ester (Example 4a, Step 2) and 1.2 g (8.9 mmol) of potassium carbonate in acetonitrile (5 mL) was added 0.17 mL (2.7 mmol) iodomethane and the mixture stirred at room temperature for 16 h. The mixture was dissolved in dichloromethane, filtered and after evaporation of the solvent the residue was chromatographed on silica gel with 60% ethyl acetate in hexanes to give 0.038 g (yield 4.5%) N-Methyl—O—(9-phenyl-9H-fluoren-9-yl)-L-serine methyl ester as an oil. $^1$H NMR (CDCl$_3$, 300 MHz) δ: 7.67 (d, 2H), 7.45–7.10 (m, 11H), 3.73 (s, 3 H), 3.35–3.15 (m, 3H), 2.37 (s, 3H), 2.06 (s, 1H); $^{13}$C NMR (CDCl$_3$, 75 MHz) 6: 173.2, 146.6, 146.4, 143.1, 140.6, 129.2, 129.1, 128.3, 128.1, 128.0, 127.1, 125.4, 125.3, 125.1, 119.9, 88.3, 63.8, 62.9, 51.7.
Step 2:

To a solution of 0.032 g (0.085 mmol) N-methyl—O—(9-phenyl-9H-fluoren-9-yl)-L-serine methyl ester from Step 1 in methanol (1 mL) was added 20% sodium hydroxide (1 mL) and the mixture stirred at room temperature for 1 h. Most of the ethanol was evaporated under vacuo, the residue suspended in water (5 mL) nd extracted with diethyl ether (2×1 mL). The alkaline aqueous phase was acidified with 20% acetic acid by cooling with an ice bath, the white precipitate was filtered, washed with water and dried in vacuo over P$_2$O$_5$ to give 0.027 g (yield 90%) N-methyl—O—(9-phenyl-9H-fluoren-9-yl)-L-serine as a white powder.

Example 6(a)

N,N-Dimethyl—O—(9-phenyl-9H-fluoren-9-yl)-L-serine
Step 1:

To a stirred solution of 0.57 g (1.6 mmol) O-(9-phenyl-9H-fluoren-9-yl)-L-serine methyl ester (Example 4a, Step 2), 0.150 g (5 mmol) paraformaldehyde and water (0.4 mL) in methanol (5 mL) was added dropwise a solution of 0.11 g (0.8 mmol) zinc chloride and 0.1 g (1.6 mmol) sodium cyanoborohydride in methanol (5 mL) at room temperature. The mixture was stirred at room temperature for 16 h, the solvent was evaporated, water (50 mL) was added and the mixture extracted with dichloromethane (3×20 mL). The combined dichloromethane extracts were washed with brine, dried (MgSO$_4$), the solvent evaporated and the residue chromatographed on silica gel with 30% ethyl acetate in hexanes to give 0.5 g (yield 81.6%) N,N-dimethyl—O—(9-phenyl-9H-fluoren-9-yl)-L-serine methyl ester as an oil. $^1$H NMR (CDCl$_3$, 300 MHz) δ: 7.68 (d, 2H), 7.40–7.10 (m, 11H), 3.73 (s, 3H), 3.40–3.15 (m, 3H), 2.29 (s, 6H); $^{13}$C NMR (CDCl$_3$, 75 MHz) 6: 171.3, 146.6, 146.5, 143.2, 140.7, 140.5, 129.1, 129.0, 128.2, 128.1, 128.0, 127.0, 125.5, 125.4, 125.3, 120.0, 119.9, 88.7, 67.7, 61.9, 51.4, 42.6, 14.2.
Step 2:

To a solution of 0.39 g (1 mmol) N,N-Dimethyl—O—(9-phenyl-9H-fluoren-9-yl)-L-serine methyl ester from Step 1 in methanol (4 mL) was added 20% sodium hydroxide (2 mL) and the mixture stirred at room temperature for 1 h. Most of the methanol was evaporated in vacuo, the residue suspended in water (10 mL) and extracted with diethyl ether (2×2 mL). The alkaline aqueous phase was acidified with 20% acetic acid by cooling with an ice bath, the white precipitate was filtered, washed with water and dried in vacuo over P$_2$O$_5$ to give 0.314 g (yield 84%) N,N-dimethyl-O-(9-phenyl-9H-fluoren-9-yl)-L-serine as a white powder. $^1$H NMR (CD$_3$OD, 300 MHz) δ: 7.87 (br s, 2H), 7.70–7.10 (m, 11H), 3.70–3.45 (m, 3H), 2.95 (s, 6H).

Example 7(a)

S-(9-Phenyl-9H-thioxanthen-9-yl)-D,L-cysteine (Photaki, I.; et al., On Cysteine and Cystine Peptides. Part V. S-Trityl- and S-Diphenylmethyl cysteine and cystine peptides., *J. Chem. Soc.* (c), 1970:2683–2697).

A mixture of 0.29 g (1 mmol) of 9-phenyl-9H-thioxanthen-9-ol (Example li) and 0.12 g (1 mmol) of D,L-cysteine were combined in a dry 50 mL flask flushed with argon. 2 mL of anhydrous trifluoroacetic acid was added and the flask was stoppered and gently swirled by hand until all the material went into solution. The dark brown solution stood for 10 to 15 minutes and was then concentrated to an oil, which was taken up in 30 mL of ether and neutralized with 15 mL of saturated NaHCO$_3$ solution. A thick precipitate formed upon shaking the mixture, which was filtered, washed with 2×15 mL of H$_2$O, 2×5 mL of acetone and 2×10 mL of ether to give light yellow powder after drying in vacuo. $_1$H NMR (dmso-d$_6$) δ: 7.51–7.15 (m, 13H), 3.31 (t, J=5.7 Hz, 1H), 2.64–2.50 (m, 2H).

In a like manner, the following additional compounds were prepared:

(b) S-[9-(3-Methylphenyl)-9H-thioxanthen-9-yl]-DL-cysteine: from 9-(3-methylphenyl)-9H-thioxanthen-9-ol (Example 1k) and D,L-cysteine as a yellow powder.

(c) S-[9-(4-Methylphenyl)-9H-thioxanthen-9-yl]-D,L-cysteine: from 9-(4-methylphenyl)-9H-thioxanthen-9-ol (Example 1p) and D,L-cysteine as a yellow powder.

(d) S-(5-Phenyl-5H-dibenzo[a,d]cyclohepten-5-yl)-D,L-cysteine: from 5-phenyl-5H-dibenzo[a,d]cyclohepten-5-ol (Example 1o) and D,L-cysteine as a yellow powder.

(e) S-[5-(3-Methylphenyl )-5H-dibenzo[a, d]cyclohepten-5-yl]-D,L-cysteine: from 5-(3-methylphenyl)-5H-dibenzo[a,d]cyclohepten-5-ol (Example 1s) and D,L-cysteine as a yellow powder.

(f) S-[5-(4-Methylphenyl)-5H-dibenzo[a,d]cyclohepten-5-yl]-D,L-cysteine: from 5-(4-methylphenyl)-5H-dibenzo[a,d]cyclohepten-5-ol (Example 1t) and D,L-cysteine as a yellow powder.

(g) S-(1 0,1 1-Dihydro-5-phenyl-5H-dibenzo[a,c] cyclohepten-5-yl)-D,L-cysteine: from 10,11-dihydro-5-phenyl-5H-dibenzo[a,d]cyclohepten-5-ol (Example 1n) and D,L-cysteine as a yellow powder.

(h) S-[9-(3-Methylphenyl)-9H-fluoren-9-yl]-D,L-cysteine: from 9-(3-methylphenyl)-9H-fluoren-9-ol (Example 1a) and D,L-cysteine as a yellow powder.

(i) S-(9-Phenyl-9H-fluoren-9-yl)-D,L-cysteine: from 9-phenyl-9H-fluoren-9-ol (Example 1b) and D,L-cysteine as a yellow powder.

(j) S-[9-(4-Methylphenyl)-9H-fluoren-9-yl]-D,L-cysteine: from 9-(4-methylphenyl)-9H-fluoren-9-ol (Example 1c) and D,L-cysteine as a yellow powder.

(k) S-(10,10-Dimethyl-9-phenyl-9,10-dihydroanthracen-9-yl)-D,L-cysteine: from 10,10-dimethyl-9-phenyl-9,10-dihydroanthracen-9-ol (Example 1j) and D,L-cysteine as a yellow powder.

(l) S-(7-phenyl-7H-benz[d,e]anthracen-7-yl )-D,L-cysteine: from 7-phenyl-7H-benz[d,e]anthracen-7-ol (Example 1v) as a yellow powder.

(m) S-(2,7-Dibromo-9-phenyl-9H-fluoren-9-yl)-D,L-cysteine: from 2,7-dibromo-9-phenyl-9H-fluoren-9-ol (Example 1u) and D,L-cysteine as a yellow powder.

Example 8(a)

$N^\alpha$-(9-Phenyl-9H-fluoren-9-yl)-DL-α,β-diaminopropionic acid

Step 1: $N^\alpha$-(9-Fuorenylmethoxycarbonyl)-$N^\beta$-(9-phenyl-9H-fluoren-9-yl)-DL-α,β-diaminopropionic acid methyl ester To a stirred solution of 0.100 g (0.36 mmol) 9-chloro-9H-fluorene (prepared by treatment of 9-phenyl-9H-fluoren-9-ol (Example 1b) with $SOCl_2$) in anhydrous dichloromethane (2 mL) was added 0.124 g of (0.36 mmol) $N^\alpha$-(9-fluorenylmethoxycarbonyl)-DL-α,β-diaminopropionic acid methyl ester hydrochloride (prepared by esterification of $N^\alpha$-(9-fluorenylmethoxycarbonyl)-DL-α,β-diaminopriopionic acid (Bachem) with methanol in the presence of 2.5 eq chlorotrimethylsilane and 0.138 g (1.08 mmol) N,N-diisopropylethylamine. The mixture was stirred at room temperature for 48 h, the solvent evaporated and the residue purified by preparative TLC with 30% ethyl acetate in hexanes to give 0.016 g (8%) $N^\alpha$-(9-fluorenylmethoxycarbonyl)-$N^\beta$-(9-phenyl-9H-fluoren-9-yl)-DL-α,β-diaminopropionic acid methyl ester as a pale yellow oil. $^1$H NMR ($CDCl_3$, 300 5 MHz) δ: 7.80–6.90 (m, 21H), 5.60 (br s, 1H), 4.50–4.00 (m, 4H), 3.60 (s, 3H), 2.44 (br s, 2H).

Step 2: $N^\beta$-(9-Phenyl-9H-fluoren-9-yl)-DL-α,β-diaminopropionic acid methyl ester Analogous to Example 4a, Step 2 deprotection of the 9-fluorenylmethoxycarbonyl (Fmoc) group of $N^\alpha$-(9-fluorenylmethoxycarbonyl)-$N^\beta$-(9-phenyl-9H-fluoren-9-yl)-DL-α,β-diaminopropionic acid methyl ester from Step 1 gave $N^\beta$-(9-phenyl-9H-fluoren-9-yl)-α,β-DL-propionic acid methyl ester. $^{13}$C NMR ($CDCl_3$, 75 MHz) δ: 175.5, 149.7, 144.7, 140.7, 128.5, 128.2, 128.1, 127.4, 126.4, 125.0, 124.9, 120.2, 72.9, 55.0, 52.3, 46.8.

Step 3: Hydrolysis of the methyl ester from Step 2 with methanolic sodium hydroxide (like in Example 4a, Step 3) provided $N^\beta$-(9-phenyl-9H-fluoren-9-yl)-DL-α,β-diaminopropionic acid as a yellow powder.

Example 9(a)

4-(9-Phenyl-9H-fluoren-9-yl)-DL-2-aminobutyric acid hydrochloride

Step 1: 3-(9-Phenyl-9H-fluoren-9-yl)propanol

To a stirred solution of 2.42 g (10 mmol) 9-phenylfluorene (prepared by reduction of 9-phenyl-9H-fluoren-9-of (Example 1b) with Zn in acetic acid according to the method of F. Ullmann, and R. von Wurstemberger, Ber., 73, 1904:37) in anhydrous tetrahydrofuran (20 mL) was added dropwise 4.8 mL (12 mmol) of a 2.5 M solution of butyllithium in hexanes at 0° C. under Ar. The mixture was stirred at room temperature for 0.5 h during which a white precipitate separated from the orange-colored solution. A solution of 2.7 g (12 mmol) of 2-(3 -bromopropoxy)tetrahydro-2H-pyran (Aldrich) was then added dropwise at 0° C., stirring was continued for 0.5 h at room temperature and the solvent evaporated. The residue was dissolved in 80% acetic acid (10 mL), the solution stirred for 16 h at 80° C., most of the solvent removed under vacuo and the residue chromatographed on silica gel with dichloromethane to provide 1.4 g (yield 48%) of 3-(9-phenyl-9H-fluoren-9-yl)propanol as an oil. $^1$H NMR ($CDCl_3$, 300 MHz) δ: 7.68 (d, 2H), 7.35–7.00 (m, 11H), 3.26 (t, 2H), 2.47 (dt, 2 h), 1.86 (s, 1H), 0.87 (dt, 2H); $^{13}$C NMR ($CDCl_3$, 75 MHz) δ: 151.4, 144.6, 140.5, 128.2, 127.5, 127.1, 126.5, 126.3, 124.1, 119.8, 62.6, 58.2, 33.7, 27.1.

Step 2: 3-(9-Phenyl-9H-fluoren-9-yl)propanal

A solution of 0.68 mL (9.6 mmol) dimethylsulfoxide in anhydrous dichloromethane (2 mL) was added dropwise to a solution of 0.4 mL (4.6 mmol) oxalyl chloride in anhydrous dichloromethane (10 mL) with stirring and cooling at −50° C. Stirring was continued for 10 min and a solution of 1.2 g (4 mmol) of 3-(9-phenyl-9H-fluoren-9H-yl)propanol (from Step 2) in anhydrous dichloromethane (2 mL) was then added dropwise at −50° C. over 10 minutes. The mixture was stirred at −50° C. for another 10 minutes, triethylamine (2.8 mL) was added dropwise and the mixture was left to reach room temperature. After addition of water (14 mL), the organic phase was separated, the water phase extracted with dichloromethane (2×3 mL), the dichloromethane phases combined, washed with brine and dried ($MgSO_4$). Evaporation of the solvent and silica gel column chromatography of the residue with 10% ethyl acetate in hexanes gave 1.0 g (yield 84%) of 3-(9-phenyl-9H-fluoren-9-yl)propanal as an oil. $^1$H NMR ($CDCl_3$, 300 MHz) δ: 9.4 (s, 1H), 7.76 (d, 2H), 7.50–7.00 (m, 11H), 2.84 (d, 2H), 1.79 (t, 2H); $^{13}$C NMR ($CDCl_3$, 75 MHz) δ: 201.7, 150.5, 144.0, 140.6, 128.4, 127.9, 127.6, 126.6, 126.4, 124.2, 120.0, 57.5, 45.7, 39.0, 29.4.

Step 3: 5-[2-(9-Phenyl-9H-fluoren-9-yl)ethyl]hydantoin

A mixture of 0.3 g (1 mmol) of 3-(9-phenyl-9H-fluoren-9-yl)propanal (from Step 2), 0.07 g (1.1 mmol) potassium cyanide and 0.23 g (2.4 mmol) ammonium carbonate in 50% aqueous ethanol (5 mL) was placed in a pressure tube and heated at 60° C. for 16 h with stirring. The reaction was then cooled to room temperature, quenched with 30% acetic acid (5 mL) and most of the solvent removed under vacuo. The residue was dissolved in ethyl acetate (100 mL), washed with water (3×10 mL), dried ($MgSO_4$) and the solvent evaporated. The residue was chromatographed on silica gel with ethyl acetate to provide 0.11 g (yield 30%) of 5-[2-(9-phenyl-9H-fluoren-9-yl)ethyl]hydantoin as a white solid. $^1$H NMR ($CD_3OD$, 300 MHz) δ: 7.79 (d, 2H), 7.40–7.00 (m, 11H), 3.86 (dd, 1 h), 2.75–2.50 (m, 2H), 1.98 (d, 1H), 1.35–0.8 (m, 3H); $^{13}$C NMR ($CD_3OD$, 75 MHz) δ: 177.8, 159.8, 152.3, 146.0, 142.1, 129.4, 128.9, 128.7, 127.6, 127.5, 125.4 121.1, 59.7, 59.4, 33.6, 27.8.

Step 4: 4-(9-Phenyl-9H-fluoren-9-yl)-DL-2-aminobutyric acid hydrochloride

A mixture of 0.1 g (0.27 mmol) of 5-[2-(9-phenyl-9H-fluoren-9-yl)ethyl]hydantoin (from Step 3) and 2N sodium hydroxide (10 mL) was heated under reflux at 120° C. for 40 h. The reaction mixture was cooled, acidified with concentrated hydrochloric acid and extracted with chloroform (3×10 mL). The combined chloroform extracts were washed with brine, dried ($MgSO_4$) and the solvent evaporated. The solid residue was washed with anhydrous diethyl ether and dried under vacuo to give 0.04 g (yield 40%) of 4-(9-phenyl-9H-fluoren-9-yl)-DL-2-aminobutyric acid hydrochloride as a pale yellow powder. $^1$H NMR ($CD_3OD$, 300 MHz) δ: 7.67 (d, 2H), 7.30–6.90 (m, 11 h), 3.56 (br s, 1H), 2.75–2.55 (m, 1H), 2.55–2.35 (m, 1H), 1.20–0.95 (m, 2H); $^{13}$C NMR ($CD_3OD$, 75 MHz) δ: 152.0, 145.8, 142.2, 142.1 129.4, 129.0, 128.8, 127.7, 127.6, 125.4, 125.3, 121.1, 59.3, 54.4, 33.7, 26.6.

Example 10

2-Amino-2-[1-(9-Phenyl-9-fluorenoxy)cyclopropyl acetic acid

Step 1: 1-Hydroxy-1-vinylcyclopropane

A solution of vinyl magnesium bromide (2eq) in anhydrous THF is cooled to 0° C. under a nitrogen atmosphere. A solution of 1-ethoxycyclopropanol (*Org. Synth., Coll. Vol. VII,* 1990, 131–134; Addition of Grignard reagents to 1-ethoxycyclopropanol in Salaun, J. *J. Org. Chem.* 1976, 41, 1237–1240) in THF is added dropwise via syringe to the reaction mixture. The resulting mixture is warmed at room temperature for 2 h and then at reflux for 2 h. The reaction mixture is hydrolysed with $H_2O$ and extracted with ether. The ethereal layers are dried ($Na_2SO_4$) and concentrated in vacuo. The crude product is distilled under reduced pressure.

Step 2: 1-(9-Phenyl-9-fluorenyl)-1-vinylcyclopropane

1-Hydroxy-1-vinylcyclopropane is added to a suspension of 9-phenyl-9-fluorenol (1eq) and AW-300 molecular sieves in anhydrous toluene under an argon atmosphere. p-Toluenesulfonic acid (catalytic amount) is added in one portion. The resulting suspension is heated at 90° C. until the disappearance of starting material is observed by thin layer chromatography. The mixture is filtered to remove the sieves. The resulting filtrate is concentrated in vacuo and the concentrate is purified by flash chromatography on silica gel using hexanes-ethyl acetate as eluent.

Step 3: 2-[1-(9-Phenyl-9-fluorenoxy)cyclopropyl]-1,2-dihydroxyethane

A solution of 1-(9-phenyl-9-fluorenyl)-1-vinylcyclopropane in acetone:$H_2O$ is treated with 4-methylmorpholine-N-oxide (2.5 eq). A catalytic amount of 4% osmium tetroxide in $H_2O$ is added. The resulting mixture is stirred at room temperature overnight. The solution is diluted with EtOAc. The resulting mixture is washed with 10%. aq sodium thiosulfate, and then brine. The EtOAc layer is dried ($Na_2SO_4$) and concentrated in vacuo. The resulting diol is purified by flash chromatography on silica gel.

Step 4: 1-(9-Phenyl-9-fluorenoxy)cyclopropane carboxaldehyde

A suspension of 2-[1-(9-Phenyl-9-fluorenoxy) cyclopropyl]-1,2-dihydroxyethane in THF:$H_2O$ is treated with $NaIO_4$ (1.1 eq). The resulting suspension is stirred at room temperature for 4h and then diluted with $H_2O$ and EtOAc. The EtOAc extract is washed consecutively with 10% aq sodium thiosulfate solution and then brine. The EtOAc layer is dried ($Na_2SO_4$) and concentrated in vacuo. The crude product is purified by filtration through a short pad of silica gel.

Step 5: 5-[1-(9-Phenyl-9-fluorenoxy)cyclopropyl] imidazolidinon-2,4-dione

A suspension of a 1-(9-Phenyl-9-fluorenoxy) cyclopropane carboxaldehyde, potassium cyanide (1.1 eq) and ammonium carbonate (2.5 eq) in 50% aqueous ethanol is heated in a sealed tube at 60° C. for 5 h. The reaction mixture is taken up in $CHCl_3$. This $CHCl_3$ mixture is extracted with $H_2O$, dried ($Na_2SO_4$) and concentrated in vacuo. The resulting concentrate is purified by flash chromatography on silica gel. The column is eluted with $CH_2Cl_2$-ethyl acetate or hexanes-ethyl acetate to afford the hydantoin.

Step 6: 2-Amino-2-[1-(9-Phenyl-9-fluorenoxy)cyclopropyl acetic acid

5-[1-(9-Phenyl-9-fluorenoxy)cyclopropyl] imidazolidinon-2,4-dione is heated in 2N NaOH at 160° C. for 2 h in a sealed tube. The reaction mixture is diluted with $H_2O$ and acidified with acetic acid. The resulting solid is recovered by filtration. Further purification is accomplished by reverse-phase chromatography or ion-exchange chromatography.

Example 11

2-Amino-4-(9-phenyl-9-fluorenyl)-3-methinylbutanoic acid.

Step 1: 3-(9-Phenyl-9-fluorenyl)-2-bromo-propene

A solution of 9-phenylfluorene in anhydrous THF is cooled to −78° C. under a nitrogen atmosphere. A solution of "BuLi in hexanes (1 eq) is added dropwise via syringe. After stirring at −78° C. for 10 min a solution of 2,3-dibromopropene (1.2eq) in THF is added dropwise via syringe. The solution is stirred at −78° C. for 1 h and then allowed to warm to room temperature. The reaction mixture is quenched by the addition of sat. aq $NH_4Cl$. The resulting mixture is extracted with ether. The organic layer is washed with $H_2O$ and then brine, dried ($Na_2SO_4$), and concentrated in vacuo. The concentrate is purified by flash chromatography on silica gel eluting with hexanes-ethyl acetate to afford the title compound.

Step 2: 3-(9-Phenyl-9-fluorenyl)-2-methenyl-propanoic acid

A solution of 3-(9-phenyl-9-fluorenyl)-2-bromo-propene in anhydrous THF is chilled to −78° C. under a nitrogen atmosphere. A solution of $^s$BuLi in hexanes (1 eq) is added dropwise via syringe. The resulting solution is stirred at −78° C. for 5 min to ensure completion of the metal-halogen exchange. A slow stream of carbon dioxide from a cylinder is passed into the mixture for 1 h. $H_2O$ is added to quench the reaction mixture and the mixture then allowed to warm to room temperature. The mixture is acidified by the dropwise addition of conc. HCl and extracted several times with ether. The combined ether layers are washed with $H_2O$, dried ($Na_2SO_4$), and concentrated in vacuo to afford the crude acid.

Step 3: 3-(9-Phenyl-9-fluorenyl)-2-methenyl-1-propanol

A solution of 3-(9-phenyl-9-fluorenyl)-2-methinyl-propanoic acid in anhydrous THF is chilled to 0° C. under a nitrogen atmosphere. A solution of 1M borane in THF (1 eq) is then added dropwise via syringe to the chilled solution. The resulting solution is allowed to warm to room temperature over the course of 2 h after the addition is completed. The reaction mixture is then cooled to 0° C. and quenched with $H_2O$. 1N NaOH is then added and the resulting mixture is stirred for 1h at room temperature. The mixture is then concentrated in vacuo. The concentrate was dissolved in ethyl acetate and washed several times with $H_2O$. The ethyl acetate layer was dried ($Na_2SO_4$) and concentrated in vacuo. The resulting concentrate is purified by flash chromatography on silica gel to furnish the alcohol.

Step 4: 3-(9-Phenyl-9-fluorenyl)-2-methinyl-propanal

A solution of oxalyl chloride (3eq) in $CH_2Cl_2$ is chilled to −78° C. under a nitrogen atmosphere. Dimethylsulfoxide (6 eq) is then added dropwise via syringe. The resulting mixture is allowed to stir at −78° C. for an additional 20 min. A solution of 3-(9-phenyl-9-fluorenyl)-2-methinyl-propanol in $CH_2Cl_2$ is added dropwise via syringe. The resulting mixture is allowed to stir at −78° C. for 45 min, and then $Et_3N$ (10 eq) is added dropwise via syringe. The resulting mixture is allowed to warm to room temperature over 30 min. Sat aq $NaHCO_3$ is added and the resulting mixture extracted several times with $CH_2Cl_2$. The combined $CH_2Cl_2$ layers are washed with $H_2O$, dried ($Na_2SO_4$), and concentrated in vacuo. The crude aldehyde is purified by filtration through a short pad of silica gel.

Step 5: 5-[2-(9-phenyl-9-fluorenyl)-2-methinylpropyl] imidazolidinon-2,4-dione

A suspension of a 3-(9-phenyl-9-fluorenyl)-2-methinyl-propanal, potassium cyanide (1.1 eq) and ammonium carbonate (2.5 eq) in 50% aqueous ethanol is heated in a sealed tube at 60° C. for 5 h. The reaction mixture is taken up in $CHCl_3$, extracted with $H_2O$, dried ($Na_2SO_4$), and concentrated in vacuo. The resulting concentrate is purified by flash chromatography on silica gel eluting with $CH_2CO_2$-ethyl acetate or hexanes-ethyl acetate to afford the hydantoin.

Step 6: 2-Amino-4-(9-phenyl-9-fluorenyl)-3-methinylbutanoic acid

5-[2-(9-phenyl-9-fluorenyl)-2-methinylpropyl] imidazolidinon-2,4-dione is heated in 2N NaOH at 160° C. for 2 h in a sealed tube. The reaction mixture is diluted with $H_2O$ and acidified with acetic acid. The resulting solid is recovered by filtration. Further purification is accomplished by reverse-phase chromatography or ion-exchange chromatography.

Example 12

2-Amino-4-(9-phenyl-9-fluorenyl)-but-3-enoic acid

Step 1: 9-Hydroxymethyl-9-phenylfluorene

To a solution of 9-phenylfluorene (13.6 mmol) in THF (40 mL) is added "BuLi (1.2 eq) dropwise at 0° C. under an argon atmosphere. The resulting mixture is stirred at 0° C. for 30 min. Paraformaldehyde (1.2 eq) is added in one portion, and the resulting mixture is allowed to stir at room temperature overnight. The reaction mixture is quenched with saturated $NH_4Cl$ solution. The resulting mixture is extracted with EtOAc. The EtOAc layer is dried ($Na_2SO_4$) and concentrated in vacuo. The concentrate is purified by flash chromatography on silica gel eluting with hexanes-ethyl acetate to isolate the alcohol.

Step 2: 9-Phenyl-9-fluorene carboxaldehyde

To a solution of oxalyl chloride (5.07 mmol) in $CH_2Cl_2$ (10 mL) at -60° C. is added DMSO (10.56 mmol) in $CH_2Cl_2$, dropwise under an argon atmosphere. The resulting mixture is stirred at -60° C. for 5 min, and a solution of 9-hydroxymethyl-9-phenylfluorene (4.4 mmol) in $CH_2Cl_2$ (2 mL) is then added dropwise over 10 minutes to the reaction mixture. The reaction mixture is allowed to stir at -50° C. for another 15 min after the addition is completed. $Et_3N$ (3 mL) is added dropwise and the resulting mixture allowed to warm to room temperature over 30 min. The reaction mixture is quenched with $H_2O$ (15 mL). The resulting mixture is extracted with $CH_2Cl_2$ (2×30 mL). The combined $CH_2Cl_2$ layers are washed with brine (1×30 mL), dried ($Na_2SO_4$) and concentrated in vacuo to afford the crude aldehyde.

Step 3: 2-(9-Phenyl-9-flourenyl)ethenyl-1,3-dioxolane

9-Phenyl-9-fluorene carboxaldehyde is dissolved in $CH_2Cl_2$ with TDA-1 {tris[2-(2-methoxyethoxy)ethyl]amine} (1 eq). 1,3-dioxolan-2-ylmethyltriphenylphosphonium bromide (1.1 eq) is added followed by a solution of sat. aq $K_2CO_3$. The mixture is warmed to reflux and stirred for 15 h. The reaction mixture is diluted with $H_2O$ and the resulting mixture is extracted with $CH_2Cl_2$. The organic layer is washed consecutively with $H_2O$, 2% aq HCl, and $H_2O$, dried ($Na_2SO_4$), and concentrated in vacuo. Purification by liquid chromatography on silica gel affords an E/Z mixture of the dioxolane.

Step 4: 3-(9-Phenyl-9-fluorenyl)propen-2-enal 2-(9-Phenyl-9-fluorenyl)ethenyl-1,3-dioxolane is dissolved in $CCl_4$. The solution is cooled to 0° C. and a solution of $Br_2$ (4 eq) in $CCl_4$ is added. A 1:1 solution of acetic acid:$H_2O$ is added and the resulting mixture is allowed to stir at room temperature until the disappearance of starting material is observed by thin layer chromatography. The reaction is mixture is diluted with $CH_2Cl_2$ and aq KOH. The mixture is extracted with $CH_2Cl_2$ several times. The combined $CH_2Cl_2$ layers were washed with aq $Na_2S_2O_3$, aq $NaHCO_3$, and $H_2O$. The $CH_2Cl_2$ layer is dried ($Na_2SO_4$) and concentrated in vacuo. The crude aldehyde is purified by filtration through a pad of silica gel.

Step 5: 5-[2-(9-phenyl-9-fluorenyl)-ethenyl]imidazolidinon-2,4-dione

A suspension of 3-(9-phenyl-9-fluorenyl)propen-2-enal, potassium cyanide (1.1 eq) and ammonium carbonate (2.5 eq) in 50% aqueous ethanol is heated in a sealed tube at 60° C. for 5 h. The reaction mixture is taken up in $CHCl_3$. This $CHCl_3$ mixture is washed with $H_2O$, dried ($Na_2SO_4$), and concentrated in vacuo. The resulting concentrate is purified by flash chromatography on silica gel.

Step 6: 2-Amino-4-(9-phenyl-9-fluorenyl)-but-3-enoic acid

5-[2-(9-phenyl-9-fluorenyl)-ethenyl] imidazolidinon-2.,4-dione is heated in 2N NaOH at 160° C. for 2h in a sealed tube. The reaction mixture is diluted with $H_2O$ and acidified with acetic acid. The resulting solid is recovered by filtration. Further purification could be accomplished by reversed phase chromatography or ion exchange chromatography.

Example 13

9-Phenyl-9-(α-ethynylglycine)fluorene

Step 1: 9-Ethynyl-9-phenylfluorene

Lithium acetylenide-ethylenediamine (10 mmol) is added to a dry flask under argon, diluted with 5 mL of HMPA, and cooled to between 0 and 5° C. with stirring. A solution of 8 mmol of 9-bromo-9-phenylfluorene dissolved in 4 mL of HMPA is added slowly to the reaction flask. The reaction mixture is warmed to room temperature and, after 2 h, 25 mL of water is slowly added. The mixture is taken up in 100 mL of ether and washed with 20mL of $H_2O$, 20 mL of brine, dried ($Na_2SO_4$) and concentrated. The product is purified by chromatography over $SiO_2$ using EtOAc/hexanes (2/98) as eluent. (Smith, W. N.; Beumel, O. F., Preparation of Alkynes with Dialkynes by reaction of monohalo- and dihaloalkanes with lithium acetylenide-ethylenediamine complex., *Synthesis*, 1974, 441–442.)

Step 2: 9-Phenyl-9-(2-N-tBOC-3-butyne-1-carbonylmethoxy)fluorene

To a dry flask under argon containing 5% 3,3',3"-phosphinidynetris-(benzenesulfonic acid), trisodium salt (TPPTS), 2.5% $Pd(OAc)_2$, 3mL of $CH_3CN$, 0.2 mL of $H_2O$, 2.5 mmol of $Et_3N$, and 1.5 mmol of 9-ethynyl-9-phenylfluorene with stirring is added 1.0 mmol α-acetyloxy-N-tBoc-glycine (Abood, Norman A.: Nosal, Roger *Tetrahedron Lett.* 1994, 35, 3669–3772), methyl ester. The reaction mixture is warmed to 50° C. for 24 h and quenched by the addition of 25 mL of $H_2O$ and 100 mL of ether. The ether fraction is washed with 10 mL of $NaHCO_3$ solution, 10 mL of $H_2O$, 10 mL of brine, dried ($Na_2CO_3$) and concentrated. The residue is purified by chromatography over $SiO_2$ using 20% EtOAc in hexanes as eluent. (Genet, J. P.; Blart, E.; Savignac, M., Palladium-catalyzed cross-coupling reactions in a homogenous aqueous medium., *Synlett*, 1992, 715–717.)

Step 3: 9-Phenyl-9-(α-ethynylglycine)fluorene

A solution of 1 mmol 9-phenyl-9-(2-N-tBOC-3-butyne-1-carbonylmethoxy)fluorene in 5 mL of 1M HCl in anhydrous EtOAc is stirred for several hours. Upon disappearance of starting material (TLC), the solvent is evaporated under reduced pressure and low temperature leaving the crude product. (Gibson, F. S.; Bergmeier, S. C.; Rapoport, H., Selective removal of an N-BOC protecting group in the presence of a tert-butyl ester and other acid-sensitive groups., *J. Org. Chem.*, 1994, 59, 3216–3218.) The residue is taken up in 5 mL of MeOH and 5 mL of 2M NaOH is added. The mixture is stirred for 4 h, concentrated to near dryness, partitioned between 10 mL of $H_2O$ and 10 mL of ether, and washed with 2×5 mL of ether. The aqueous fraction is neutralized with glacial acetic acid and the product is isolated by filtration and washed with 2×3 mL of $H_2O$ and dried in vacuo.

Example 14

Assay of Transport Via GlyT-1 or GlyT-2 Transporters

This example illustrates a. method for the measurement of glycine uptake by transfected cultured cells.

Cells transiently transfected with human GlyT-1C (see Kim, et al., *Molecular Pharmacology*, 45, 1994:608–617) and human GlyT-2 (the sequence of the human GLYT-2 is described by Albert et al. in co-pending U.S. application Ser. No. 08/700,013, filed Aug. 20, 1996; the rat GlyT-2 is described by Liu et al., J. Biological Chemistry, 268, 1993:22802–22808) were washed three times with HEPES buffered saline (HBS). The cells were then incubated 10 minutes at 37° C., after which a solution containing 50 nM [$^3$H]glycine (17.5 Ci/mmol) and either (a) no potential competitor, (b) 10 mM nonradioactive glycine or (c) a concentration of a candidate drug was added. A range of concentrations of the candidate drug was used to generate data for calculating the concentration resulting in 50% of the effect (e.g., the $IC_{50}$'s which are the concentration of drug inhibiting glycine uptake by 50%). The cells were then incubated another 10 minutes at 37° C., after which the cells were aspirated and washed three times with ice-cold HBS. The cells were harvested, scintillant was added to the cells, the cells were shaken for 30 minutes, and the radioactivity in the cells was counted using a scintillation counter. Data were compared between the same cells contacted and not contacted by the candidate agent, and between cells having GlyT-1 activity versus cells having GlyT-2 activity, depending on the assay being conducted.

All exemplified compounds of the invention were tested for inhibition of glycine transport via GlyT-2 and displayed a $pIC_{50}$ in the range of about 4.0–8.5. Selectivity for inhibition of glycine transport via GlyT-2 versus GlyT-1 was at least about 0.5 to 4.5 log units for all of the exemplified compounds.

Example 15

Assay of Transport via the GAT-1 Transporter

This example illustrates a method for the measurement of γ-amino butyric acid (GABA) uptake by transfected cultured cells.

Cells transiently transfected with GAT-1 (Nelson, H., Mandiyan, S., and Nelson N. *FEBS Lett.* 269 1990:181–184) and plated in 24-well tissue culture plates were washed twice with HEPES buffered saline (HBS). 200 μl of HBS was added to each well, after which 25 μl of competing drug or vehicle was added and the cells incubated for 15 minutes at room temperature. A range of concentrations of the candidate drug was used to generate data for calculating the concentration resulting in 50% of the maximum effect (i.e. the IC50 value, which is the concentration of drug inhibiting GABA uptake by 50%). 25 μl of a 25 nM solution of [3H]GABA (89 Ci/mmol) was then added. Separate wells were treated with 25 μl of 25 nM [3H]GABA, with or without cold GABA at 10 μM. The cells were then incubated another 15 minutes at room temperature, after which the supernatant was aspirated and the cells washed twice with ice-cold HBS. The cells were solubilized in scintillant, shaken for 30 minutes, and the radioactivity in the cells was counted using a scintillation counter. Exemplified compounds of the invention were tested for inhibition of GABA transport via GAT-1 and certain of these A displayed a $pIC_{50}$ in the range of from about 4 to about 7.

We claim:

1. A compound according to Formula I:

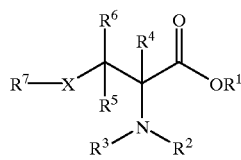

I or a prodrug or pharmaceutically acceptable salt, solvate or hydrate thereof wherein:

$R^1$ is selected from the group consisting of H, alkyl and the counter ion for a basic addition salt;

X is selected from the group consisting of $CR^9R^{10}$, S, O, SO, $SO_2$, NH and N-alkyl;

$R^2$, $R^3$, $R^8$, $R^9$ and $R^{10}$ are independently selected from the group consisting of H and alkyl;

$R^5$ and $R^6$ are independently selected from the group consisting of H, alkyl and phenyl, or, alternatively, $R^5$ and $R^6$ together may form a methylene group or a 3- to 6-membered spirocyclic group;

wherein, when X is $CR^9R^{10}$, one or both pairs of $R^5$ and $R^9$ or $R^6$ and $R^{10}$ may be linked to form a double or triple bond;

$R^7$ is

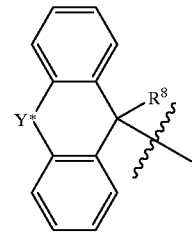

III* which are all optionally substituted, at nodes other than $R^8$, with 1–4 substituents independently selected from the group consisting of alkyl, halo, aryl (which may be substituted as for $R^8$), trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2NH$alkyl, —$SO_2N$(alkyl)$_2$ and 1,2-methylenedioxy;

wherein $R^8$ is selected from the group consisting of H, alkyl, benzyl, cycloalkyl, indanyl and an optionally substituted aryl group, wherein the optional substituents are independently selected from 1–4 members of the group consisting of alkyl, halo, aryl, trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2NH$alkyl, —$SO_2N$(alkyl)$_2$ and 1,2-methylenedioxy;

Y* is selected from the group consisting of a direct bond, $CH_2$, CH-alkyl, C(alkyl)$_2$, C=O, —CH—$CH_2$—, and —CH=CH—.

2. A compound according to claim 1 wherein $R^5$ and $R^6$ are independently selected from the group consisting of H, alkyl and phenyl.

3. A compound according to claim 2, wherein $R^1$, $R^2$, $R^3$ and $R^4$ are independently selected from the group consisting ot H and methyl.

4. A compound according to claim 3, wherein $R^1$, $R^2$, $R^3$ and $R^4$ are all H.

5. A compound according to claim 2, wherein $R^1$ is Na.

6. A compound according to claim 1, wherein one of $R^5$ and $R^6$ is H and the other is methyl.

7. A compound according to claim 2, wherein X is selected from the group consisting of $CH_2$, $CR^9R^{10}$, S, O, and NH.

8. A compound according to claim 7, wherein X is O.

9. A compound according to claim 1, wherein the compound is selected from the group consisting of:

2-Amino-2-[1-(9-Phenyl-9-fluorenoxy)cyclopropylacetic acid;

2-Amino-4-(9-phenyl-9-fluorenyl)-3-methinylbutanoic acid;

2-Amino-4-(9-phenyl-9-fluorenyl)-but-3-enoic acid;

9-Phenyl-9-(α-ethynylglycine)fluorene; and.

10. A pharmaceutical composition, comprising a pharmaceutically acceptable carrier and, in a therapeutically effective amount, a compound of Formula VI

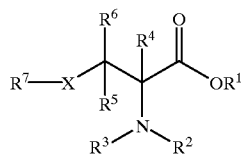

VI or a prodrug or pharmaceutically acceptable salt, solvate or hydrate thereof wherein:

$R^1$ is selected from the group consisting of H, alkyl and the counter ion for a basic addition salt;

X is selected from the group consisting of $CR^9R^{10}$, S, O, SO, $SO_2$, NH and N-alkyl;

$R^2$, $R^3$, $R^4$, $R^9$ and $R^{10}$ are independently selected from the group consisting of H and alkyl;

$R^5$ and $R^6$ are independently selected from the group consisting of HH alkyl and phenyl, or, alternatively, $R^5$ and $R^6$ together may form a methylene group or a 3- to 6-membered spirocyclic group;

wherein, when X is $CR^9R^{10}$, one or both pairs of $R^5$ and $R^9$ or $R^6$ and $R^{10}$ may join to form a double or triple bond;

$R^7$ is:

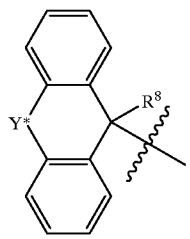

III* which are all optionally substituted, at nodes other than $R^8$, with 1–4 substituents independently selected from the group consisting of alkyl, halo, aryl (which may be substituted as for $R^8$), trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2$NHalkyl, —$SO_2N(alkyl)_2$ and 1,2-methylenedioxy;

wherein $R^8$ is selected from the group consisting of H, alkyl, benzyl, cycloalkyl, indanyl and an optionally substituted aryl group, wherein the optional substituents are independently selected from 1–4 members of the group consisting of alkyl, halo, aryl, trifluoromethyl, trifluoromethoxy, nitro, cyano, amino, mono-alkylamino, di-alkylamino, alkoxycarbonyl, alkylcarbonyl, alkoxythiocarbonyl, alkylthiocarbonyl, alkoxy, alkylS-, phenoxy, —$SO_2NH_2$, —$SO_2$NHalkyl, —$SO_2N(alkyl)_2$ and 1,2-methylenedioxy;

Y* is selected from the group consisting of O, S, SO, NH, N-alkyl, a direct bond, $CH_2$, CH-alkyl, $C(alkyl)_2$, C=O, —$CHCH_2$—, and —CH=CH—.

11. A method for treating a patient having a medical condition for which inhibition of glycine transport is indicated, comprising the step of administering to the patient a pharmaceutical composition as defined in claim 10.

12. A method according to claim 11, wherein the medical condition is associated with increased or decreased muscle contraction.

13. A method for treating a patient having a medical condition for which a GlyT-2 glycine transport inhibitor is indicated, comprising the step of administering to the patient a pharmaceutical composition according to claim 11 which contains a compound of Formula VI which inhibits glycine transport via both GlyT-1 and GlyT-2.

14. A method for treating a patient having a medical condition for which a GlyT-2 glycine transport inhibitor is indicated, comprising the step of administering to the patient a pharmaceutical composition according to claim 10 which contains a compound of Formula VI which inhibits glycine transport via GlyT-2 and which also inhibits GABA uptake.

15. A method according to claim 11 in which the medical condition is pain or spasticity.

16. A method for treating a patient having a CNS condition comprising administering to the patient a pharmaceutical composition containing a compound which inhibits glycine transport via GlyT-2 and which also inhibits GABA uptake.

17. A method for treating a patient having a CNS condition comprising administering to the patient a pharmaceutical composition containing a compound which inhibits glycine transport via both GlyT-1 and GlyT-2.

18. A method according to claim 13 in which the medical condition is pain.

19. A method according to claim 14 in which the medical condition is spasticity.

* * * * *